US006277268B1

(12) United States Patent
Khesin et al.

(10) Patent No.: US 6,277,268 B1
(45) Date of Patent: Aug. 21, 2001

(54) SYSTEM AND METHOD FOR MONITORING GASEOUS COMBUSTIBLES IN FOSSIL COMBUSTORS

(75) Inventors: Mark J. Khesin, North Andover, MA (US); Alexander A. Ivantotov, Solnechnaya (RU)

(73) Assignee: Reuter-Stokes, Inc., Twinsburg, OH (US)

(*) Notice: Subject to any disclaimer, the term of this patent is extended or adjusted under 35 U.S.C. 154(b) by 0 days.

(21) Appl. No.: 09/412,149

(22) Filed: Oct. 5, 1999

Related U.S. Application Data

(60) Provisional application No. 60/107,484, filed on Nov. 6, 1998.

(51) Int. Cl.[7] ........................ G01N 27/417; G01N 27/409

(52) U.S. Cl. ........................ 205/784.5; 204/424; 204/429; 431/76

(58) Field of Search .................................... 204/424–429; 431/76, 13; 205/784.5, 784

(56) References Cited

U.S. PATENT DOCUMENTS 3,936,648 2/1976 Cormault et al. .
4,039,844 8/1977 MacDonald .
4,101,403 * 7/1978 Kita et al. ............................ 204/429
4,253,404 3/1981 Leonard .
4,260,363 4/1981 Cratin, Jr. .
4,296,727 10/1981 Bryan .
4,370,557 1/1983 Axmark et al. .
4,562,529 12/1985 Drummond .
4,639,717 1/1987 De Meirsman .
4,709,155 11/1987 Yamaguchi et al. .
4,828,673 5/1989 Maeda .
4,866,420 9/1989 Meyer, Jr. .
4,885,573 12/1989 Fry et al. .
4,901,247 2/1990 Wakimoto et al. .
4,923,117 5/1990 Adams et al. .

(List continued on next page.)

FOREIGN PATENT DOCUMENTS 0 476 601 3/1992 (EP) .
0 581 451 2/1994 (EP) .
PCT WO 97/24560 7/1997 (WO) .

OTHER PUBLICATIONS

Brochure for Miracle Sensor, MPV–2 Combustion Diagnostic System/CO Monitor, unknown.*
M.J. Khesin, et al., "Smart Flame Scanners—Myth or Reality?", American Power Conference, Chicago, Apr. 1995.
M.J. Khesin, "Combustion Diagnostics based on Frequency Spectra Analysis", American Flame Research Committee, Montery, CA, Oct. 1995.
Forney Corporation, "OptiFlame Burner Diagnostic System", 1996 Month N/A.
M.J. Khesin, et al., "Demonstration of New Frequency–Based Flame Monitoring System", American Power Conference, Chicago, Apr. 1996.

(List continued on next page.)

*Primary Examiner*—Robert J. Warden, Sr.
*Assistant Examiner*—Kaj K. Olsen
(74) *Attorney, Agent, or Firm*—Wolf, Greenfield & Sacks, P.C.

(57) ABSTRACT

A Nernstian-type gas sensor for monitoring changes in a concentration of oxygen present in an environment. One embodiment includes a mass of solid-electrolyte material, and first and second electrodes. The first and second electrodes are each in fluid communication with the environment and are arranged to generate a signal therebetween indicative of a difference between an oxygen concentration at the first electrode and an oxygen concentration at the second electrode. The sensor may be free of a temperature control device.

16 Claims, 14 Drawing Sheets

ANALYZED GAS
408
102
405
404
410
401
407
403
403
410
401
406
404
410
409
402

U.S. PATENT DOCUMENTS

| | | | |
|---|---|---|---|
| 5,073,769 | 12/1991 | Kompelien . | |
| 5,076,780 | 12/1991 | Erdman . | |
| 5,077,550 | 12/1991 | Cormier . | |
| 5,107,128 | 4/1992 | Davall et al. . | |
| 5,191,220 | 3/1993 | Innes . | |
| 5,249,954 | 10/1993 | Allen et al. . | |
| 5,257,496 | 11/1993 | Brown et al. . | |
| 5,280,756 | 1/1994 | Labbe . | |
| 5,296,112 * | 7/1978 | Seger et al. | 204/424 |
| 5,332,386 | 7/1994 | Hosome et al. . | |
| 5,496,450 | 3/1996 | Blumenthal et al. . | |
| 5,501,159 | 3/1996 | Stevers et al. . | |
| 5,599,179 | 2/1997 | Lindner et al. . | |
| 5,796,342 | 8/1998 | Panov . | |
| 5,798,946 | 8/1998 | Khesin . | |
| 5,827,415 | 10/1998 | Gür et al. . | |
| 6,103,098 * | 8/2000 | Omara et al. | 205/784.5 |

OTHER PUBLICATIONS

M.J. Khesin, et al., "Application of a Flame Spectra Analyzer for Burner Balancing", Sixth International Joint ISA POWID/EPRI Controls and Instrumentation Conference, Baltimore, Jun., 1996.

M.J. Khesin, et al., "Demonstration of New Flame Monitoring System at a Pilot–Scale Gas–Fired Combustion Test Facility", American Flame Research Committee, International Symposium, Baltimore, Md, Sep., 1996.

MK Engineering, Inc., "System may boost combustion efficiency", Industry Watch, Sep. 1996.

M.J. Khesin, et al., "Demonstration Tests of New Burner Diagnostic System on a 650 MW Coal–Fired Utility Boiler", presented at the American Power Conference, Chicago, Apr. 1997.

M.J. Khesin, et al., "Application of a New Burner Diagnostic System for Coal–Fired Utility Boilers", presented to the Joint ISA/EPRI Symposium, Jun., 1997, Knoxville, TN.

MK Engineering, Inc., "Combustion Diagnostic System", illustrated brochure distributed Jan., 1998.

MK Engineering, Inc., "Application of MPV–1 Combustion Diagnostic System—A Case Study, Application on a 650 MW Coal–Fired Unit" Jan., 1998.

MK Engineering, Inc., "MPV–1 Combustion Diagnostic System for Tangential Boilers", Jan., 1998.

MK Engineering, Inc., "MPV–1 Combustion Diagnostic System", distributed Feb., 1998.

"Algorithms convert chaos into efficiency", text as printed in Personal Engineering and Instrumentation, Apr., 1998.

M.J. Khesin et al., "Combustion Control—New Environmental Dimension"; pp. 1262–1266; Proceedings of the American Power Conference. (Date Unknown).

M.J. Khesin et al., "Fluctuations in the Oxidising Potential of Combustion Products as an Indicator of Losses Due to Unburnt Gases", pp. 40–42; 1978 Teploenergetika vol. 25 Month N/A.

M.J. Khesin et al., MPV Combustion Diagnostic and Optimization System; The Mega Symposium, EPRI–DOE–EPA Combined Utility Air Pollutant Control Symposium; Aug. 1999.

MK Engineering, Inc.; Combustion Diagnostic System/CO Monitor "Miracle Sensor", distributed Jan. 1998.

* cited by examiner 813
810
815
102
807
800
801
805
806
816
814

SYSTEM AND METHOD FOR MONITORING GASEOUS COMBUSTIBLES IN FOSSIL COMBUSTORS

This application claims the benefit of provisional application serial No. 60/107,484, filed Nov. 6, 1998.

BACKGROUND OF THE INVENTION

1. Field of the Invention

The present invention relates to novel gas sensors that may be used in conjunction with boilers, furnaces, or other combustors.

2. Discussion of Related Art

In numerous industrial environments, a hydrocarbon fuel is burned in a combustor (e.g., a boiler or furnace) to produce heat to raise the temperature of a fluid. The fluid may, for example, be water which is heated to generate steam to drive a turbine generator that provides power. Such industrial combustors typically employ an array of many individual burner elements to combust the fuel. In these combustors, various post-flame combustion control systems, such as overfire air, staging air, reburning systems, and selective non-catalytic reduction systems, can be employed in the post-flame zone to enhance the efficiency of the combustor. For the combustor to operate efficiently and to produce an acceptably complete combustion having byproducts that fall within the limits imposed by environmental regulations and design constraints, all of the individual burners should be operating cleanly and efficiently, and all post-flame combustion control systems should be properly balanced and adjusted.

Emissions of unburned carbon, nitrous oxides, carbon monoxide or other byproducts commonly are monitored to ensure compliance with environmental regulations. The monitoring of emissions heretofore has been done, by necessity, on the aggregate emissions from the combustor (i.e., the entire burner array—taken as a whole). Some emissions, such as the concentration of gaseous combustibles in hot flue gases, are difficult and/or expensive to monitor on-line and continuously. These emissions are typically measured on a periodic or occasional basis. When a particular combustion byproduct is found to be produced at unacceptably high concentrations, the combustor should be adjusted to restore proper operations. However, measurement of aggregate emissions, or measurement of emissions on a periodic or occasional basis, provides little, if any, useful information regarding what particular combustor parameters should be changed to effect such an adjustment.

SUMMARY OF THE INVENTION

According to one aspect of the present invention, a Nernstian-type gas sensor includes a mass of solid-electrolyte material, and first and second electrodes. The first and second electrodes are disposed on the mass of solid-electrolyte material to generate a signal therebetween indicative of a difference between an oxygen concentration at the first electrode and an oxygen concentration at the second electrode. Each of the first and second electrodes is in fluid communication with the environment.

According to another aspect of the invention, a method for monitoring changes in a concentration of oxygen present in an environment includes providing at least one Nernstian-type gas sensor including a mass of solid-electrolyte material, and at least first and second electrodes. Each of the first and second electrodes is disposed on the mass of solid-electrolyte material and is in fluid communication with the environment. A signal is generated between the at least first and second electrodes in response to changes in the concentration of oxygen in the environment.

According to another aspect of the invention, an apparatus for monitoring changes in a concentration of gas molecules of at least a first type in an environment includes a mass of material and first and second electrodes. The mass of material is permeable to ions formed when gas molecules of the first type are ionized. The first and second electrodes are arranged on the mass of material such that, when a concentration of the gas molecules of the first type at the first electrode is different than a concentration of the gas molecules of the first type at the second electrode, gas molecules of the first type are ionized at the first electrode to form ions which flow from the first electrode to the second electrode via the mass of material and are recombined at the second electrode to form gas molecules of the first type, thereby generating a signal between the first and second electrodes. Each of the first and second electrodes is in fluid communication with the environment.

According to another aspect of the invention, a method for monitoring changes in a concentration of gas molecules of at least a first type in an environment includes providing at least one Nernstian-type gas sensor including a mass of material that is permeable to ions formed when gas molecules of the first type are ionized, and at least first and second electrodes each arranged on the mass of material and each in fluid communication with the environment. A signal is generated between the at least first and second electrodes in response to changes in the concentration of the gas molecules of the first type in the environment.

According to another aspect of the invention, a Nernstian-type gas sensor includes a mass of solid-electrolyte material, and first and second electrodes. Each of the first and second electrodes is disposed on the mass of solid-electrolyte material to generate a signal therebetween indicative of a difference between an oxygen concentration at the first electrode and an oxygen concentration at the second electrode. The sensor is free of a temperature control device.

According to another aspect of the invention, a method for monitoring changes in a concentration of oxygen in an environment includes providing at least one Nernstian-type gas sensor including a mass of solid-electrolyte material and at least first and second electrodes disposed on the mass of solid-electrolyte material, wherein the at least one sensor is free of a temperature control device. A signal is generated between the at least first and second electrodes in response to changes in the concentration of oxygen in the environment.

According to another aspect of the invention, a method for calibrating a gas sensor includes supplying each of a first gas having a first profile and a second gas having a second profile, which is different that the first profile, to the gas sensor in a predetermined sequence. The gas sensor or a signal analyzer associated therewith is adjusted based upon an output signal of the gas sensor to calibrate the gas sensor.

According to another aspect of the invention, an apparatus for calibrating a gas sensor includes a switching system and a sequencer. The switching system is in fluid communication with each of a first tank having a first predetermined gas profile and a second tank having a second predetermined gas profile. The sequencer causes the switching system to supply gas from each of the first and second tanks to the gas sensor in a predetermined sequence.

According to another aspect of the invention, a method for calibrating a gas sensor includes supplying gas such that a concentration of molecules of at least a first type in the gas changes during a time interval. The gas supplied during the time interval is provided to the gas sensor so that the gas sensor generates a first signal in response to the change in the concentration of the first type of molecules in the gas during the time interval. The gas supplied during the time interval is also provided to a reference sensor so that the reference sensor generates a second signal in response to the change in the concentration of the first type of molecules in the gas during the time interval. At least one characteristic of the first signal is compared to at least one characteristic of the second signal, and the gas sensor or a signal analyzer associated therewith is adjusted based upon the comparison of the at least one characteristic of the first signal and the at least one characteristic of the second signal to calibrate the gas sensor.

DETAILED DESCRIPTION

1. Overview

Figure 1A:
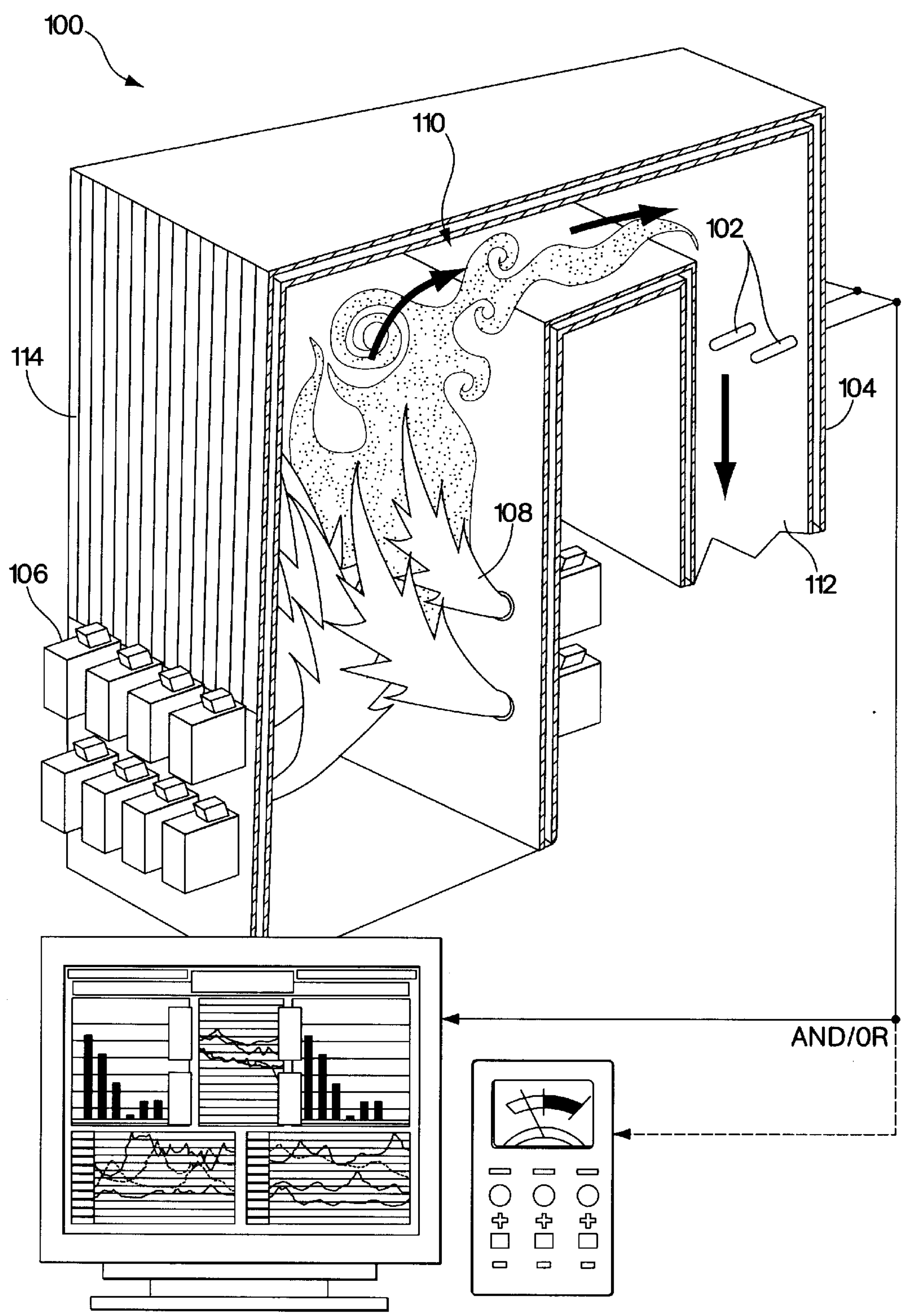
FIGS. 1A and 1B illustrate an example of a boiler having solid-electrolyte sensors positioned therein to produce signals indicative of levels of gaseous combustibles.

To achieve the goal of stable and efficient operation of any combustion apparatus, it is useful to achieve continuous, on-line monitoring of various combustion variables and their distribution profiles in different combustion zones. When such monitoring is accomplished effectively, individual burners as well as post-flame combustion controls may be adjusted to achieve optimum relationships between the fuel and air flows, an optimum distribution of individual air flows and reburning fuel flows, and an optimization of other boiler adjustments, thereby increasing the efficiency of the combustor significantly.

It is known to employ an in-situ oxygen sensor to monitor the concentration of oxygen in a combustor. Typically, such a sensor employs a pair of porous metal (e.g., platinum) electrodes disposed adjacent one another on opposite sides of a solid electrolyte (e.g., yttria ($Y_2O_3$) stabilized zirconia ($ZrO_2$) (YSZ)) element, with one of the electrodes (a reference electrode) being surrounded by a gas having a predetermined oxygen concentration, and the other electrode (a sensing electrode) being exposed to the gas being monitored. Examples of such sensors are described, for example, in U.S. Pat. Nos. 5,296,112 and 5,827,415, each of which is hereby incorporated herein by reference in its entirety. In these sensors, when the solid electrolyte element is heated to a sufficient temperature (e.g., above 600° C.), it becomes permeable to oxygen ions. Therefore, when the concentration of oxygen molecules is greater at one of the electrodes than at the other, oxygen ions will migrate from one of the electrodes to the other, with the electrodes serving as catalytic surfaces that enable oxygen molecules to become oxygen ions. The electron imbalance resulting from this flow of oxygen ions and the ionization/deionization occurring at the respective electrodes generates a voltage between the electrodes that is a function of the ratio of the partial pressures of oxygen at the two electrodes, as well as the temperature of the solid electrolyte material. The voltage generated between the two electrodes is defined by the so-called "Nernst" equation, as follows:

$$E=\frac{RT}{4F}\times \mathrm{Ln}\left(\frac{P1}{P2}\right)+C$$

wherein:

E=the voltage out,

T=the absolute temperature of the sensor,

R=the Universal Gas Constant,

F=Faraday's Constant,

P1=the partial pressure of oxygen in the reference gas,

P2=the partial pressure of oxygen in the monitored gas,

C=a constant for each individual sensor, and

Ln(P1/P2) is the natural logarithm of the ratio P1/P2.

As can be noted, the only variables in the Nernst equation are E, T, P1, and P2. When the partial pressure of oxygen in the reference gas (P1) is held constant, the signal E output by such a prior art sensor is therefore affected only by: (1) changes in the partial pressure of oxygen in the measured gas P2, and (2) changes in the temperature T of the sensor. By eliminating the effect of the sensor's temperature T on the value of the voltage E, the voltage E output by such a sensor responds only to changes in the value P2 and can therefore be used as an accurate indicator of the concentration of oxygen in the measured gas (i.e., E=f(P2)). The effect of a Nernstian-type gas sensor's temperature T on the value of the voltage E output therefrom is typically eliminated using one of two techniques. According to one technique, a heater is provided within the sensor, and is the heater activated selectively to maintain the sensor at a constant temperature T. In accordance with another technique, a thermocouple is disposed within the sensor to measure the sensor's temperature T, and the voltage E is adjusted to compensate for changes in the temperature T. As used herein, the term "temperature control device" refers to any device, circuitry, hardware, software, or any combination thereof, that is employed to eliminate the effect of the temperature T of a Nernstian-type gas sensor on the voltage E output thereby, using either of the two above-described techniques.

With Nernstian-type gas sensors that employ at least one porous catalytic electrode (e.g., a porous platinum electrode), when gaseous combustibles come into contact with the catalytic electrode under proper conditions, they are caused to combine chemically with oxygen in a combustion-type reaction to form non-combustible by-products. For example, two carbon monoxide molecules (2CO) may combine with one oxygen molecule ($O_2$) to form two carbon dioxide molecules ($2CO_2$) (i.e., $2CO + O_2 = 2CO_2$), or two hydrogen molecules ($2H_2$) may combine with one oxygen molecule ($O_2$) at the electrode to form two water molecules ($2H_2O$) (i.e., $2H_2 + O_2 = 2H_2O$). As used herein, the term "gaseous combustible" refers to any gaseous molecule that is capable of being combined chemically with oxygen in a combustion-type reaction. Because of this chemical reaction between gaseous combustibles and oxygen at the catalytic electrode, a rise in the level of gaseous combustibles causes additional oxygen molecules near the electrode to be consumed, thereby decreasing the concentration of oxygen at the electrode and correspondingly changing the voltage output by the sensor. Similarly, a decrease in the level of gaseous combustibles near the electrode causes fewer oxygen molecules near the electrode to be consumed, thereby increasing the concentration of oxygen at the electrode and correspondingly changing the voltage output by the sensor.

In the flue gas in the post flame zone (explained below) of a combustor, carbon monoxide (CO) is typically the most prevalent gaseous combustible present. In fact, carbon monoxide typically accounts for more than ninety-five percent of the gaseous combustibles present in the flue gas. Therefore, the output signal from a Nernstian-type gas sensor sensing the flue gas of combustor may serve as a reliable indicator of the level of CO present therein.

The signals from prior art Nernstian-type gas sensors include two components: (1) intensity ("the DC component"), and (2) fluctuating frequency ("the AC component"). The DC component, according to the Nernst equation, is a function of several parameters, including sensor temperature and oxygen concentration in the analyzed and reference gases. The DC component is typically the component of interest in systems employing these sensors. Therefore, the fluctuating AC component is commonly filtered from the output signal of an oxygen sensor because it is considered to be useless noise.

Our experimental testing of boilers, supported by theoretical analysis, has demonstrated that the fluctuational AC component of an in-situ oxygen sensor may be used as an indicator of combustion efficiency. This topic is discussed, for example, in two articles: (1) Khesin, M. J., Johnson A. J., "Combustion Control: New Environmental Dimension," American Power Conference, Chicago, 1993; and (2) Khesin, M. J., Ivantotov, A. A., "Fluctuations of Flue Gas Oxygen as Indicator of Combustibles," Teploenetgetika, 1978, 5, each of which is hereby incorporated herein by reference. As discussed in these articles, an output signal generated by a solid-electrolyte, in-situ oxygen sensor can be used to monitor gaseous combustibles by correlating the fluctuating AC component of such a signal with gaseous combustibles.

In order to exploit the phenomenon described in references (1) and (2) discussed above in a practical and useful manner, however, serious technical difficulties needed to be overcome. These difficulties included high operating temperatures (e.g., above eight-hundred degrees Celsius (° C.)), gradual reduction of the catalytic capacity of sensor electrodes, inconsistency of results, and uncertainty of signal processing algorithms used to obtain such results. Embodiments of the present invention aim to overcome these difficulties by offering an effective sensor design, and an effective and universal method and system for monitoring gaseous combustibles in a combustor.

In one embodiment of the present invention, one or more solid-electrolyte oxygen sensors are positioned in the flue gas flow in the post-flame zone (described below in connection with FIG. 1A) of a combustor to measure fluctuations in the oxygen concentration of the flue gas. The fluctuations measured by these sensors may be used to calculate values which correlate with real-time levels of gaseous combustibles.

In one embodiment of the invention, each sensor includes a solid-electrolyte (e.g., YSZ) element and at least two metal (e.g., platinum) electrodes associated therewith. In accordance with an aspect of the present invention, each of the electrodes may be in fluid communication with a common gaseous environment so that oxygen molecules in the common environment can reach either of them. The electrodes may be configured and arranged so that the degree of fluid communication between the common gaseous environment and one of the electrodes is different than the degree of fluid communication between the common gaseous environment and the other electrode. In this manner, when the oxygen concentration in the common environment changes from a first level to a second level, the rate at which the oxygen concentration at one of the electrodes changes from the first level to the second level is different than the rate at which the oxygen concentration at the other electrode changes from the first level to the second level. In other words, each of the electrodes may be configured and arranged so that there is a time constant associated therewith that determines how quickly the oxygen concentration level at that electrode rises or falls to a new oxygen concentration level in the common environment.

Any of a number of different relationships involving a time constant may exist between the oxygen concentration at each electrode and the oxygen concentration in the common environment, and the invention is not limited to any particular type of relationship. One example of a relationship between the oxygen concentration at an electrode and the oxygen concentration in the common environment is an exponential relationship involving a time constant Tc, such as:

$$C_E = C_C + \Delta C_C * (1 - e^{-t/Tc}),$$

wherein:

$C_E$=the concentration of oxygen at the electrode, $C_C$=the concentration of oxygen in the common environment, $\Delta C_C$=the change in concentration of oxygen in the common environnent, e=the exponential operator, t=the time elapsed since the change in oxygen concentration occurred, and Tc is a time constant specific to the electrode.

The electrodes are in fluid communication with the common environment by different "degrees" when the time constants $T_C$ of the two electrodes are different. The electrodes may be configured and/or arranged in any of numerous ways so that their time constants Tc differ from one another, and the invention is not limited to any particular technique for accomplishing the same. In various illustrative embodiments, for example, this goal may be achieved simply by employing electrodes that differ in their design, material and/or characteristics. For example, the electrodes may have different geometries, may be coated by materials having different porosities, may be coated by different materials, and/or may be coated by different amounts of a material, e.g., a porous, high-temperature epoxy.

When the electrodes are configured and arranged so as to have different time constants, a measured potential between the electrodes represents primarily the fluctuational AC component of the oxygen concentration in the measured gas, rather than representing both the AC and DC components, or primarily the DC component, as was done with the prior art sensors described above in which one of a pair of sensors was surrounded by a gas having a predetermined oxygen concentration. What constitutes a suitable difference between the time constants of the electrodes may vary from application to application, and the invention is not limited to any particular difference between the time constants. In various embodiments, for example, the time constants of the electrodes may differ from one another by some value between a few (e.g., two) milliseconds and several (e.g., ten) minutes.

It should be appreciated that the novel sensor configuration described herein is not limited to applications wherein the concentration of oxygen is monitored, as this sensor may also find applications in sensing the concentration of numerous other types of gases, e.g., carbon monoxide (CO), nitrous oxide (NOx), etc., as well.

In one embodiment of the invention, the output signal from an in-situ oxygen sensor is fed to a signal analyzer, e.g., a programmed computer, where it is analyzed and used to generate one or more combustion parameters that are correlated with combustion conditions.

In another embodiment, the signal is processed in the frequency domain by using a frequency domain amplitude spectrum of the signal to generate an extremum function (as described below), and one or more combustion parameters are calculated based upon one or more characteristics of the extremum function so generated. In another embodiment, the signal is processed in the time domain (as described below) by analyzing one or more characteristics of a time domain representation of the signal during a selected time interval. In still another embodiment, the signal is processed both in the frequency and time domains, and the results of calculations in each domain are combined to yield one or more combustion parameters. The levels of the gaseous combustibles may then be estimated using a combination of these calculated combustion parameters, along with limiting conditions which may depend, for example, on the temperature, level of oxygen, and/or combustibles in the controlled gas. These limiting conditions may, for example, be determined from the DC component of the sensor signal. It should be appreciated that this aspect of the invention relating to novel techniques for processing signal(s) from oxygen sensor(s) in the frequency and/or time domains to yield combustion parameters may be employed either with the prior art oxygen sensors described above which surround one electrode with a reference gas, with the oxygen sensors described above in which at least two electrodes are each in fluid communication with a common gaseous environment, or with any other type of sensor which generates a signal that includes a fluctuational AC component representing a concentration of a gas (e.g., oxygen) or other fluid.

When a single sensor is used, it generates a signal indicative of the level of gaseous combustibles at the particular point where the analyzed gas comes in contact with the sensor. The signal from such a single sensor may provide a sufficient amount of information to permit the operation of a small, single-burner industrial combustor to be optimized. When several sensors are inserted into the flue gas flow (e.g., across the width) of a combustor, the outputs of the sensors represent a distribution profile of the gaseous combustibles within the combustor. Such a profile can be utilized for combustor balancing and optimization. For example, individual burners and/or post-flame combustion systems can be adjusted to alter the generated profile until it reflects that optimal and balanced combustion conditions have been achieved. An understanding of (1) how the profile should appear when such optimal and balanced combustion conditions have been achieved, and (2) how individual burners and/or post-flame combustion systems affect different aspects of the profile may be obtained through empirical measurements. This boiler balancing and optimization may be particularly usefuil for larger, multi-burner combustion systems.

2. Example Embodiment

Figure 1B:
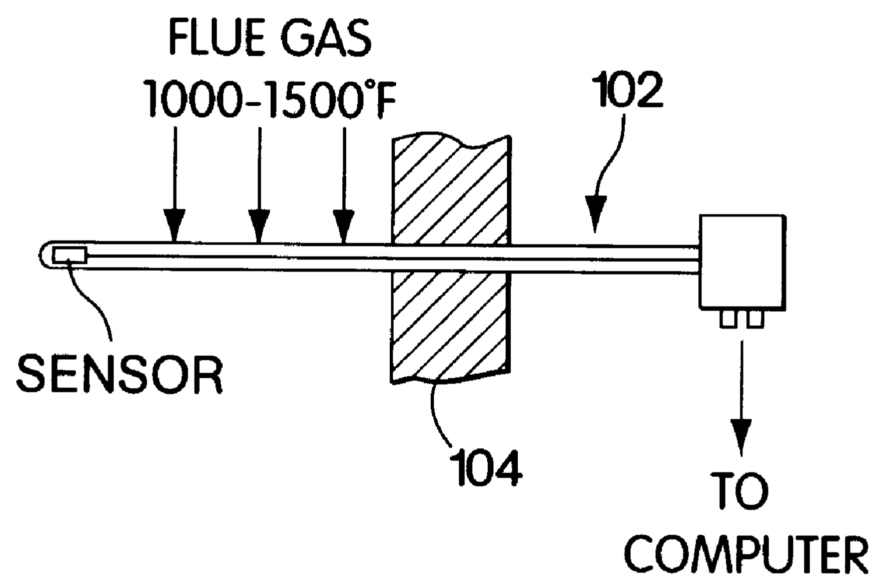

Turning to FIGS. 1A and 1B, shown there is a cross-sectional illustration of a combustor 100 and typical sighting of several in-situ oxygen sensors 102 positioned across the width of a flue gas duct 104 of the combustor 100 to monitor the stream of hot flue gases flowing therethrough. The sensors 102 may, for example, be solid-electrolyte sensors which measure the concentration of (and/or changes in the concentration of) oxygen in the flue gases, or any other sensors capable of generating a signal indicative of the concentration of (and/or changes in the concentration of) one or more other types of gases present in the flue gases. In practice, any number of sensors 102 may be installed (preferably in a row) across the width of the flue gas duct 104. The sensors may also be arranged in a vertically-oriented row, or in a grid-like manner or other effective pattern to monitor the distribution profile of gaseous combustibles.

In some embodiments, the combustor 100 may be more than one, two or even three hundred feet tall. As shown in FIG. 1A, the combustor 100 may include a plurality of combustion devices (e.g., combustion device 106) which mix fuel and air to generate flame in a flame envelope 108 within the combustor 100. The combustion devices may be any of numerous types of flame-producing devices, and the invention is not limited to a particular type of combustion device. According to one embodiment, for example, the combustion devices may include burners (e.g., gas-fired burners, coal-fired burners, oil-fired burners, etc.). In such an embodiment, the burners may be arranged in any manner, and the invention is not limited to any particular arrangement. For example, the burners may be situated in a wall-fired, opposite-fired, tangential-fired, or cyclone arrangement, and may be arranged to generate a plurality of distinct flames, a common fireball, or any combination thereof. Alternatively, a combustion device called a "traveling grate" may be employed to generate flame within the combustor 100. A traveling grate is a device that uses a flame-resistant grate resembling a conveyor belt to convey coal or another fuel into a combustion area of the combustor 100.

As defined in a publication by the National Fire Protection Association (NFPA) of Quincy, Mass., entitled "NFPA 85C, an American National Standard," p.85C-11, Aug. 6, 1991, "flame" refers to "the visible or other physical evidence of the chemical process of rapidly converting fuel and air into products of combustion," and a "flame envelope" refers to "the confines (not necessarily visible) of an independent process converting fuel and air into products of combustion."

Referring to FIG. 1A, when the combustion devices 106 in the combustor 100 are actively burning fuel, two distinct locations can be identified within the combustor 100: (1) a flame envelope 108, and (2) a so-called "post-flame" zone 110, which is the zone outside of the flame envelope 108 spanning some distance toward the exit 112. Outside the flame envelope 108, hot combustion gases and combustion products may be turbulently thrust about. These hot combustion gases and products, collectively called "flue gas," make their way away from the flame envelope 108 toward an exit 112 of the combustor 100. Water or another fluid (not shown) may flow through the walls (e.g., wall 114) of the combustor 100 where it may be heated, converted to steam, and used to generate energy, for example, to drive a turbine. In the embodiment shown, the sensors 102 are located in the post-flame zone 110 of the combustor 100. It should be appreciated, however, that the invention is not limited in this respect, and that the sensors 102 alternatively may be disposed in the flame envelope 108 if constructed to withstand the harsh, high-temperature environment thereof.

As mentioned above, in one embodiment of the invention, the fluctuational component gaseous combustibles. The reason for this correlation is believed to be as follows. Individual burner flames comprise a multitude of eddies of various sizes inside and around the flame envelope 108. These eddies contribute to generating the familiar flame flicker at various frequencies as a result of turbulent mixing at the edges of the fuel and air jets. The eddies are transformed in the combustion process, and move in the general direction of the furnace exit 112. The overall combustion turbulence reflects the process of energy transfer from large-scale eddies to smaller and smaller eddies, down to the molecular level. The rate of the mixing process and the resulting intensity of these turbulent activities determines combustion stability and directly relates to the processes of formation and destruction of gaseous combustibles. Most of these chaotic, turbulent activities begin and occur in the flame envelope 108.

Some turbulent activities do take place in the flue gas flow of the post-flame zone 110. However, small eddies associated with combustion kinetics (i.e., small-scale, high-frequency turbulence) tend to dissipate quickly and generally do not reach the post-flame zone 110. Typically, only large eddies (i.e., large-scale, low frequency turbulence) are present in the post-flame zone 110. This low-frequency turbulence reflects combustion variables (e.g., an amount of unburned carbon and other combustibles), particularly those associated with the secondary combustion processes that are influenced by post-flame combustion control systems, such as overfire air and reburning. A turbulent stream of hot flue gases passing into the flue gas duct 104 carries products of incomplete combustion, including gaseous combustibles. As mentioned above, these gaseous combustibles travel in the turbulent flue gas flow as relatively large eddies. Each time the proper conditions occur, such as the presence of a catalyst and a high temperature (e.g., between 1000 and 1500° F.) near a sensor 102, the gaseous combustibles are caused to burn and the oxygen concentration near the sensor is reduced. These fluctuations in the oxygen concentration near the sensor's electrode(s) cause pulses to be generated in the signal output by the sensor 102. The frequency and amplitude of these pulses characterizes the level of gaseous combustibles present in the analyzed flue gas flow.

The relationship between the sensor output signal and levels of gaseous combustibles may be affected by various factors, including operating combustion parameters, physical parameters, and chemical reactions. In order to more accurately monitor this multi-variable process, according to one embodiment of the invention, two or more mathematically different signal processing algorithms are employed simultaneously to analyze the signal output by the sensor, and the results of the several algorithms are combined.

Figure 2A:
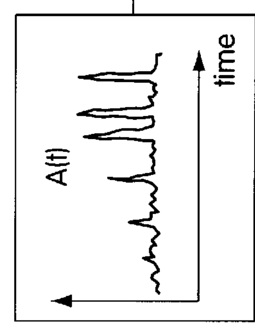
FIG. 2 illustrates a typical signal from a solid-electrolyte sensor and signal processing calculations that may be performed thereon.
Figure 2B:
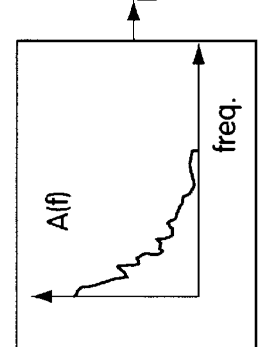
Figure 2C:
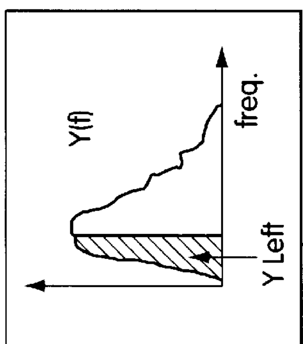

FIGS. 2A–E illustrate an example of a method for processing a typical raw output signal A(t) generated by a sensor 102 positioned in the post-flame zone 110 of a combustor 100 at the correct temperature conditions (e.g., between 1000 and 1500° F.). According to the illustrated embodiment of the invention, signal processing calculations are conducted both in the frequency and time domains. In the frequency domain, the raw unfiltered output signal A(t) (FIG. 2A) of the sensor 102 is converted into a frequency domain amplitude spectrum A(f) (FIG. 2B), and is further processed into a bell-shaped extremum function Y(f) (FIG. 2C). Examples of techniques for converting a frequency domain amplitude spectrum into a suitable extremum function Y(f) are described below in connection with FIG. 5, as well as in U.S. Pat. No. 5,798,946, and in co-pending patent application Ser. No. 09/097,959 still pending, each of which is hereby incorporated herein by reference in its entirety.

Once generated, the extremum function Y(f) may be analyzed in any of numerous ways to yield a combustion parameter which can be correlated with a combustion variable (e.g., a level of gaseous combustibles) based on empirical measurements. In the embodiment of FIG. 2C, a combustion parameter P(f) is generated by calculating the total area $Y_{left}$ under the curve Y(f) on the left-hand side of the extremum function Y(f). It should be appreciated that this is only one example of how the parameter P(f) can be calculated, and any of numerous alternative techniques can be used to generate one or more combustion parameters dependent on one or more characteristics of the extremum function Y(f).

Figure 2D:
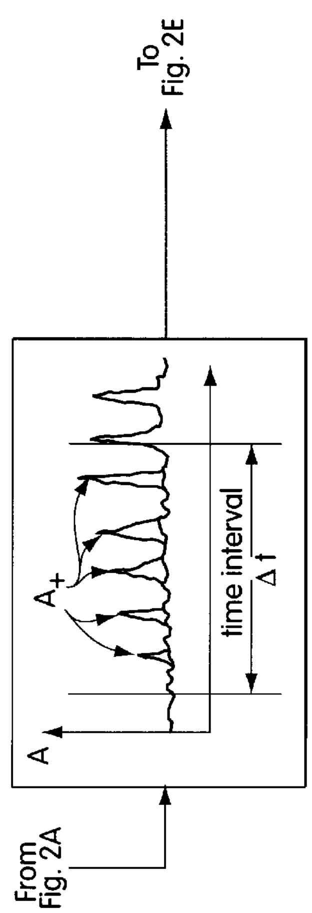
Figure 2E:
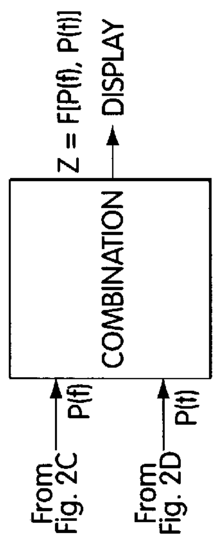

In the time domain, a time interval Δt (FIG. 2D) of the raw unfiltered input signal A(t) of a duration sufficient for statistical analysis may be selected. As with the extremum function Y(f), the signal A(t) during the time interval Δt may be analyzed in any of a number of ways to yield one or more combustion parameters indicative of one or more combustion variables (e.g., a level of gaseous combustibles), and the invention is not limited to any particular technique for analyzing the time-domain signal A(t). As shown in FIG. 2D, in one illustrative embodiment, after AC coupling, the total area $A_+$ under the positive peaks of the signal A(t) may be calculated to generate a combustion parameter P(t). The time domain parameter P(t) (FIG. 2D) may be calculated, for example, by multiplying the number of positive peaks $m_+$ by the average amplitude of all of the peaks within the time interval Δt. In embodiments wherein sensor(s) that produce signals including significant DC components (e.g., the prior art sensors described above in which one of a pair of electrodes is surrounded by a reference gas) are employed, the time domain calculations may be performed so as to measure the area $A_+$ beneath the positive peaks, or another characteristic of the time domain signal, in relation to a DC offset value, e.g., an average DC value during the time interval Δt. Additional examples of alternative approaches that may be used to evaluate a signal in the time domain to obtain parameters indicative of combustion variables based thereon are described in U.S. Pat. No. 5,796,342, which is hereby incorporated herein by reference in its entirety, as well as in co-pending patent application Ser. No. 09/097,959 still pending.

Empirical experimental results may be used to correlate each of the values P(f) and P(t) (FIG. 2E) with levels of gaseous combustibles (which, in fossil-fuel combustors, comprise mostly CO). Either of these values therefore may be used independently to provide an indication of one or more combustion variables. However, it has been recognized that both of these correlations are non-linear, at least slightly different, and depend on various operating conditions, particularly on sensor temperature and oxygen concentration near the sensor electrode(s). Therefore, in one embodiment of the invention, in order to form a more effective, representative and reliable indicator of levels of gaseous combustibles, a combined parameter (i.e., a function of at least two mathematically different signal processing algorithms, such as Z=F [Y(f);Y(t)]) is calculated.

Under normal operating conditions, fossil combustion systems are operated to maintain levels of gaseous combustibles as low as possible. The maximum allowable level of CO emissions is commonly regulated such that when it exceeds a certain limit, for example one-hundred parts per-million (ppm), severe penalties may be applied. Usually, during normal operation of fossil combustors in the power industry, the CO level is maintained well below 1000 ppm. However, unusually high levels of CO occasionally may occur during load changes or emergency situations. When the CO level becomes very high (e.g., greater than 2000 ppm), the calculated signal Z may saturate and provide incorrect information because of a possible decline in fluctuations of the raw signal A(t) (FIG. 2A).

Figure 3:
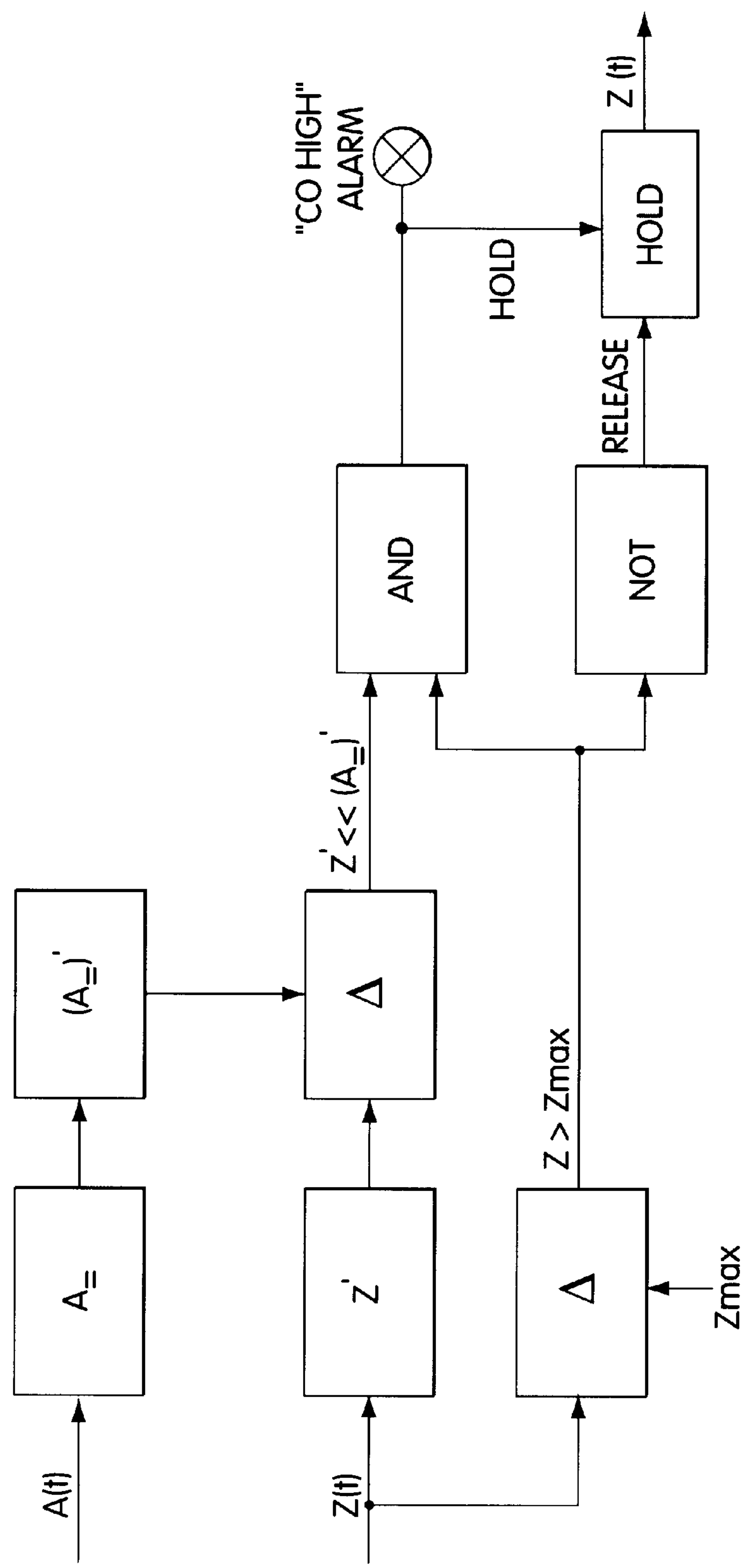
FIG. 3 illustrates an example of a possible implementation of a protection support system to avoid negative effects of signal saturation at high levels of CO.

In order to prevent incorrect information from being generated when excessive levels of gaseous combustibles, (e.g., CO levels greater than 2,000–4,000 ppm) are present, the calculated signal Z is supported by the DC component ($A_=$) of the raw signal A(t). FIG. 3 illustrates one possible implementation of such support based on comparisons involving a predetermined value Zmax, the signal Z, and the derivatives (Z' and $A_='$) of the signals Z and $A_=$. As shown, when Z>Zmax and $Z' << A_='$, an alarm is initiated and the signal Z is locked. When Z<Zmax, the signal Z is released to normal operation. Basically, this system operates as a measuring range limiter.

Figure 4B:
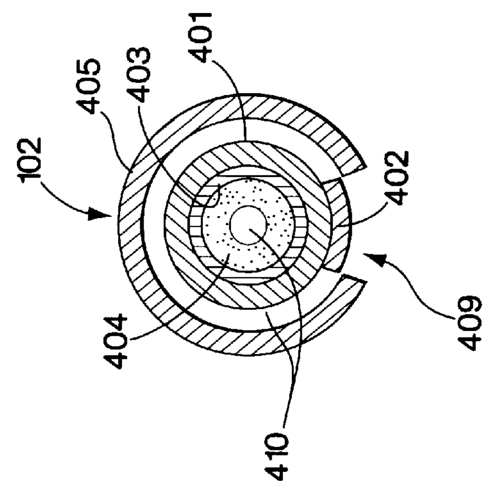
FIGS. 4A–B illustrate an example of a solid-electrolyte sensor designed to measure fluctuations of oxygen potential in a stream of hot flue gas in accordance with one aspect of the invention.
Figure 4A:
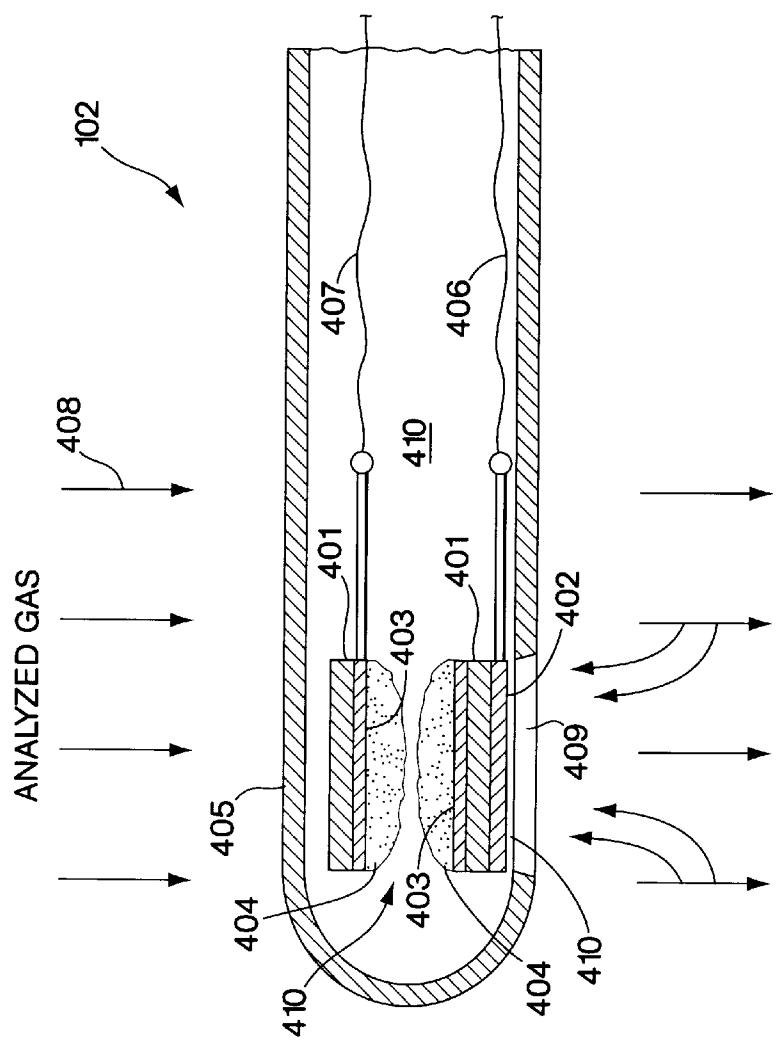

FIGS. 4A–B show side and front cross-sectional views, respectively, of an illustrative implementation of a solid-electrolyte sensor 102 to measure fluctuations in the oxygen potential in a stream of hot flue gas 408 in accordance with one aspect of the invention. As shown, the sensor 102 includes a test tube-shaped element 405 that forms an environment 410 therein. The environment 410 is in fluid communication with the flue gas 408 via an opening 409 in the element 405. Disposed within the environment 410 is a small tube 401 of a solid electrolyte material (e.g., YSZ) with at least two electrodes 402 and 403 arranged thereon. One of the electrodes (e.g., the electrode 402) may serve as a sensing electrode and may be made of a porous catalytic conductor (e.g., platinum), and the other electrode (e.g., the electrode 403) may serve as a reference electrode and may be made of the same material, or of a non-catalytic conductor.

As shown, each of the electrodes 402 and 403 may be configured and arranged so as to be in fluid communication with the environment 410 within the element 405. It should be appreciated that the environment 410 need not be partially enclosed within a structure such as the test tube-shaped element 405. Instead, it may be any environment in which a gas (or other fluid) to be analyzed may be present. For example, the test tube-shaped element 405 may be excluded from the embodiment of FIGS. 4A–B so that the environment 410 with which each of the electrodes 402 and 403 is in fluid communication is simply an area surrounding the electrodes 402 and 403 in which the analyzed gas 408 is present.

In the illustrative embodiment shown, a mass of damper material 404 (e.g., a mass of high-temperature porous epoxy resin) is disposed atop at least a portion the reference electrode 403 so as to reduce the degree by which the reference electrode 403 is in fluid communication with the common environment 410, thereby increasing the time constant of the electrode 403. With the damper material 404 present on the reference electrode 403, in response to a change in the oxygen concentration level within the common environment 410, the oxygen concentration at the sensing electrode 402 will rise almost immediately to the oxygen concentration level within the common environment 410, whereas the oxygen concentration at the reference electrode 403 will rise toward the new oxygen concentration level within the common environment 410 at a defined rate. In other words, in the embodiment shown, the sensing electrode 402 has a very small time constant Tc (e.g., a fraction of a second) associated with it (because it is directly exposed to the common environment 410), whereas the reference electrode 403 has a different, much larger time constant Tc associated with it (because the degree of fluid communication between the reference electrode 403 and the common environment 410 is limited by the mass of damper material 404). Therefore, when the analyzed gas 408 enters the common environment 410 via the opening 409 in the element 405, the potential between the electrodes 402 and 403 is indicative of the rate of change of the oxygen concentration of the analyzed gas 408.

It should be appreciated that this difference in time constants of the electrodes can be achieved in any of a number of alternative ways, and the invention is not limited to the particular technique described. In various alterative embodiments, for example, electrodes made of different materials, at having different materials disposed thereon, and/or electrodes having different porosities or geometries, on having materials or structures with different porosities or geometries disposed thereon or arranged with respect thereto, may be employed to provide a difference between the time constants of the electrodes. In various alternative embodiments, for example, one of the electrodes may be disposed within a compartment that is in fluid communication with the common environment via only a small channel or duct and is otherwise separated from the common environment, or the fluid access path between one of the electrodes and the common environment may be partially blocked or partially restricted by a solid element or a porous mass of material such as a wire or cloth mesh.

It should also be appreciated that, in embodiments wherein the sensor is disposed so as to monitor gas flowing thereby, the electrodes need not be configured and/or arranged so that the measured gas reaches the two electrodes at different rates, but instead (or additionally) may be configured and/or arranged so that the gas monitored by the sensor physically reaches one of the sensor's electrodes prior to reaching the other.

In the embodiment of FIGS. 4A–B, conductors 406 and 407 are connected to the electrodes 402 and 403 to provide the signal representing the potential between the electrodes 402 and 403 to a signal processing circuit (not shown) for analysis. The signal carried by the conductors 406 and 407 may, for example, be used as the signal A(t) of FIG. 2, and may be used to calculate the combustion parameters P(f) and P(t) of FIG. 2. Potential "side effects" of temperature or other factors may be compensated by using two or more reference electrodes of different types.

It should be noted that, in the embodiment of FIGS. 4A–B, the sensor 102 does not require a heater or other temperature control device to keep the temperature T of the solid electrolyte material 401 constant, or to otherwise eliminate the effect of changes in the temperature T of the solid electrolyte material 401 on the value of the voltage (E) (from the Nernst equation) produced by the sensor 102. Such a temperature control device is not required in the illustrative embodiment shown because it is the fluctuational AC component of the output signal of the sensor 102 that is of interest to the signal analyzer described herein. It is therefore not necessary that the non-fluctuational DC component of the signal be the same each time the measured gas 408 has a particular oxygen concentration, as in the prior art Nernstian-type oxygen sensors described above. Therefore, the sensor 102 may be employed as described herein without bringing the temperature of the tube 401 to any particular level or compensating for deviations in the temperature T from a particular level, so long as the temperature of the probe rises sufficiently to permit the solid electrolyte material to become permeable to oxygen ions. It should be appreciated, of course, that the lack of a temperature control device is not a critical feature of the invention, and that some embodiments of the invention may, in fact, employ heaters or other temperature control devices therein.

Figure 5:
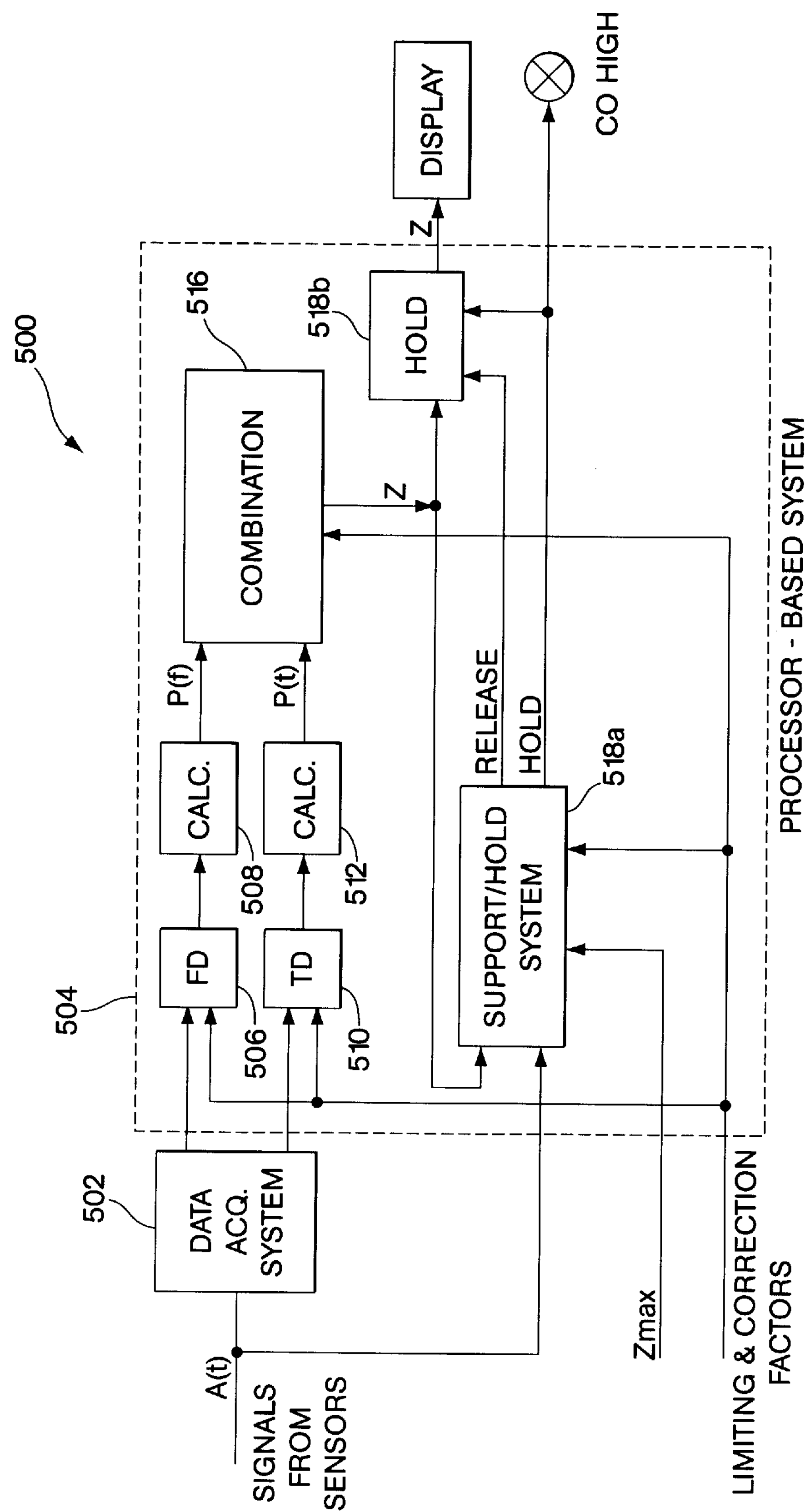
FIG. 5 illustrates an example of a system architecture used in accordance with an illustrative embodiment of the present invention.

FIG. 5 illustrates an example of a signal analyzer 500 in accordance with an illustrative embodiment of the present invention. In the embodiment shown, input signal(s) from the sensor(s) (not shown), usually in the analog form, are supplied to a data acquisition subsystem (DAS) 502 which receives, isolates, amplifies, and digitizes the input signals. From the DAS 502, the signals (in a digitized form) may be supplied to a processor unit 504 which performs various calculations in both the time and frequency domains, and may generate a combined output signal Z as a combination of P(f) and P(t), as discussed above. The processor unit 504 may be implemented using hardware, firmware, software, or any combination thereof. In one embodiment, the processor unit 504 is a programmed general-purpose digital computer or CPU (or multiple CPUs) such as a conventional personal computer.

As shown in FIG. 5, the processor unit 504 may include: (A) a frequency domain unit 506 and a calculation unit 508 to calculate the parameter P(f); (B) a time domain unit 510 and a calculation unit 514 to calculate the parameter P(t); and (C) a combination unit 516 to combine the parameters P(f) and P(t).

In one illustrative embodiment, the frequency domain unit 506 includes Fast-Fourier transform (FFT) unit (not shown) that receives digital data from data acquisition system 502, and converts the data into a frequency-domain amplitude spectrum $A=f_1(F)$(i.e., the amplitude "A" is equal to the function "$f_1$" of the frequency "F"). The frequency domain unit 506 may then generate a curve $Y=f_2(F,A)$(i.e., the variable "Y" is equal to the function "$f_2$" of the frequency "F" and the amplitude "A") having at least one extremum value, i.e., a point on the curve where its first derivative is equal to zero, as follows. First, a three-dimensional surface "S" may be defined by an equation having both amplitude (A) and frequency (F) as variables, i.e., $S=f_3(A,F)$. For example, surface S may be defined as $S=m*A^i+n*F^j$, wherein m, n, i, and j are variables defined by the user according to combustor variables, e.g., fuel type, combustor load, etc., and "*" is the multiplication operator.

Next, the frequency-domain amplitude spectrum $A=f_1(F)$ at a given moment in time may be mapped onto the surface $S=f_3(A,F)$ to define the curve $Y=f_2(A,F)$ in the surface S. This may accomplished, for example, by calculating a value of $S=f_3(A,F)$ for each point in the frequency-domain amplitude spectrum $A=f_1(F)$ at the given moment in time. In one embodiment, the surface S has only a positive extremum value, i.e., a point on surface S where partial derivatives in the directions of the A and F coordinate axes are both equal to zero and where partial second derivatives in the directions of the A and F coordinate axes are negative. Therefore, according to this embodiment, the curve Y in the surface S will generally have only one positive extremum value, i.e., a point on the curve Y where its first derivative is equal to zero and its second derivative is negative. In alternative embodiments, the surface S may additionally or alternatively have a negative extremum value, i.e., a point on surface S where partial derivatives in the directions of the A and F coordinate axes are both equal to zero and where partial second derivatives in the directions of the A and F coordinate axes are positive. In such embodiments, the curve Y in the surface S may additionally or alternatively have a negative extremum point, i.e., a point on the curve Y where its first derivative is zero and its second derivative is positive.

According to one embodiment of the invention, the frequency domain unit 506 may identify the coordinates of the extremum point(s) of the curve Y, and pass these coordinates to the calculation unit 508. After receiving the coordinates of the extremum point, the calculation unit 508 may calculate various relationships involving these coordinates. For example, as discussed above in connection with FIG. 2D, the total area $Y_{left}$ under the curve Y(f) on the left-hand side of the extremum function Y(f) (i.e., on the low-frequency side of the identified extremum point) may be calculated, and the value $Y_{left}$ may be passed to the combination unit 516 as the parameter P(f).

The time domain unit 510 may receive digital data from data acquisition system 502, and accumulate a number of samples during a particular time interval. The calculation unit 512 may then calculate a time domain parameter P(t) based upon one or more characteristics of the accumulated samples. For example, as discussed above in connection with FIG. 2D, the calculation unit 512 may calculate total area $A_+$ under the positive peaks of the signal A(t) to generate the combustion parameter P(t). As discussed above, in one illustrative embodiment, the time domain parameter P(t) may be calculated by multiplying the number of positive peaks $m_+$ by the average amplitude of all of the peaks within the time interval $\Delta t$.

As shown in FIG. 5, the processor unit 504 may additionally include a support/hold system 518*a–b* which continuously compares the output Z of the combination unit 516 with a preset allowable maximum Zmax, which depends on the specifics of the particular application (e.g., type of fuel, type of combustor, temperature level, etc.), and which may be set based upon experimental results. One example of a support/hold system that may be used as the support/hold system 518*a–b* is discussed above in connection with FIG. 3. The support/hold system may, for example, initiate a temporary limiting action, as described above in connection with FIG. 3, in case of excessive CO levels.

It should be understood that the various units and systems of the processor unit 504 may be implemented in various ways such as, for example, by software executed on a CPU or dedicated processor, and that the various units need not be, although they possibly can be, implemented using separate hardware components.

Figure 6:
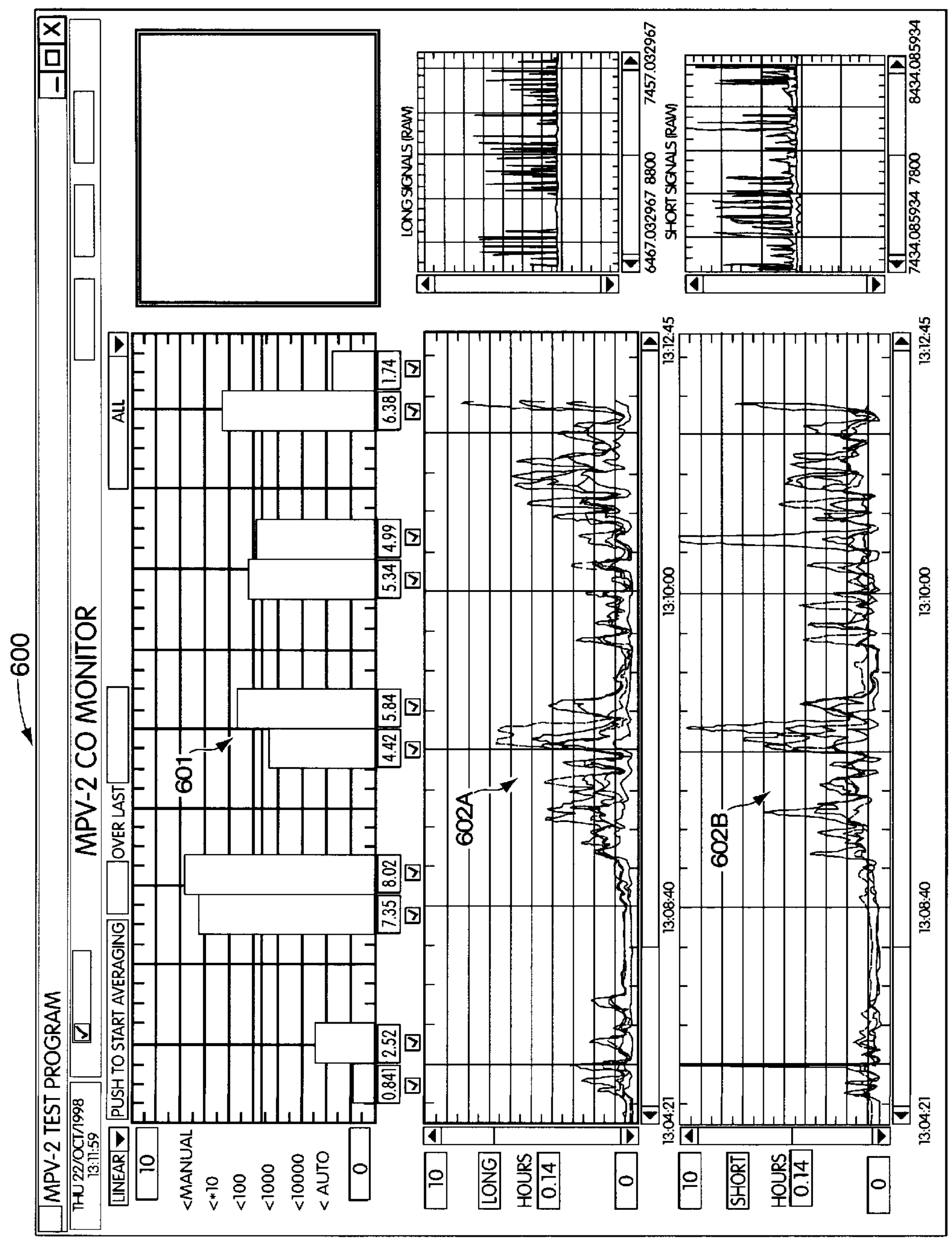
FIGS. 6 and 7 illustrate examples of system displays that may be presented to a user in accordance with an illustrative embodiment of the present invention.

FIG. 6 shows an illustrative example of a system display 600 which can provide an operator with continuous on-line information 601 regarding the concentration and distribution of combustibles in a large coal-fired boiler, e.g., the combustor 100 of FIG. 1A. As shown, the raw signals 602*a* and 602*b* from the sensors 102 may also be displayed to enable the operator to monitor the status of the sensors 102. If one of the sensors 102 becomes plugged or damaged, the operator will immediately see that its raw signal 602 has become abnormally high or low.

Figure 7:
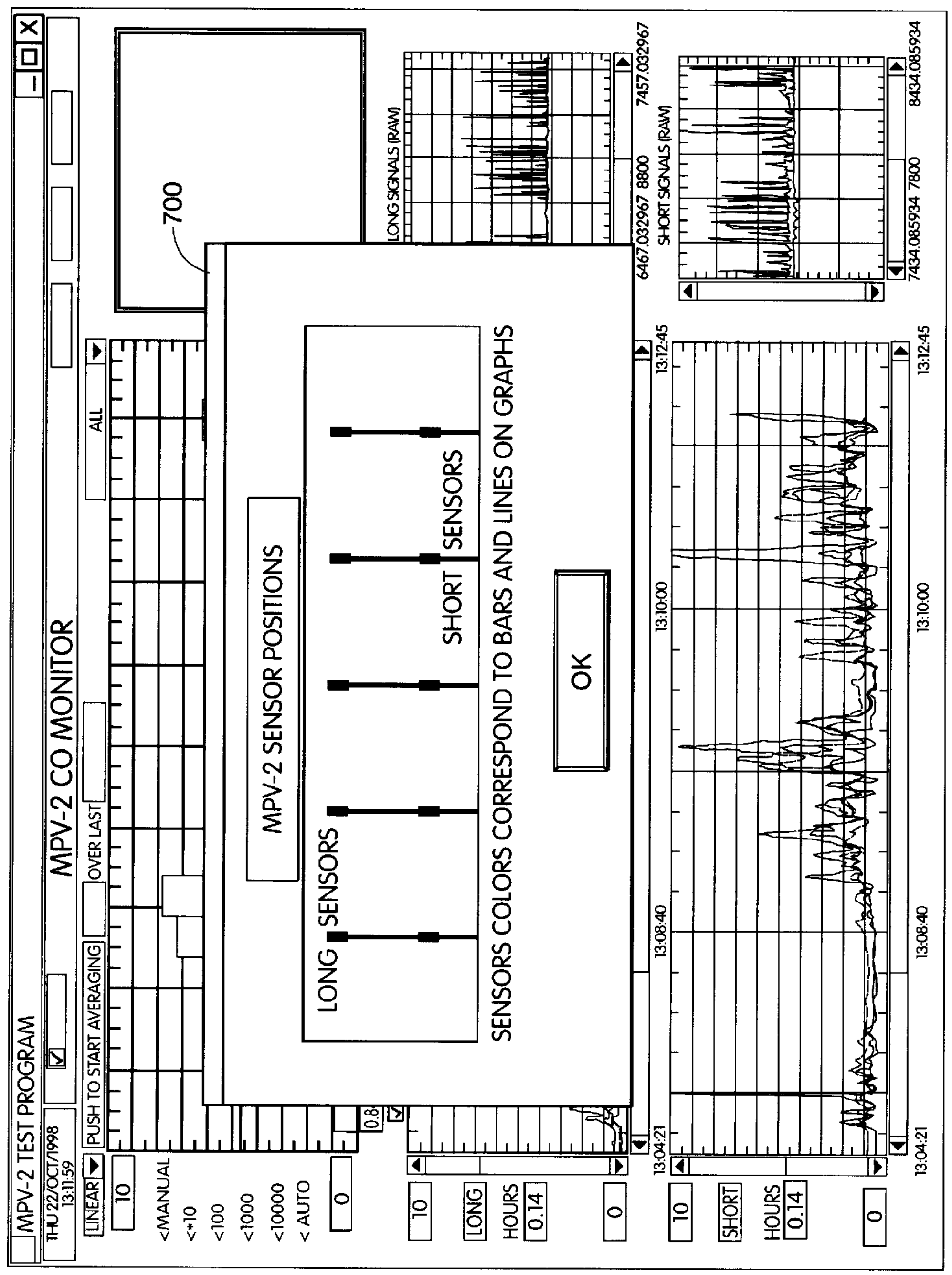

In large combustors, a need may exist to monitor the profile of combustibles at several locations within the combustor. It may be desirable, for example, to monitor the levels of combustibles at various locations within the central portions of the flu-gas duct of a combustor so as to monitor local imbalances of combustible levels at these locations. FIG. 7 illustrates an exemplary system display 700 which shows physical locations of sensors (e.g., sensors 102) within a combustor (e.g., combustor 100 of FIG. 1A). In the FIG. 7 example, the physical locations of ten sensors in a three-hundred MW boiler are shown. In very large combustors, the distance across the width of the flu-gas duct can become quite large, thereby rendering it difficult to position probes at relatively large distances from the walls of the combustor. For example, there may be a need to position several probes as far as twenty feet or more from a wall of a combustor so as to establish a grid-like arrangement of probes to map the distribution profile of combustibles.

When sensors are mounted on the distal ends of relatively long probes, the difference in thermal expansion rates between the probe body (e.g., a metal pipe), and the wires extending between the sensor and the proximal end of the probe (i.e., the end adjacent the combustor wall) can cause a number of technical problems. The probe body may, for example, heat up more quickly than the wires disposed therein because the probe body is exposed directly to the extremely hot (e.g., 1500+° F.) environment within the combustor, whereas the sensor wires are isolated from the hot combustor environment via the probe body. Therefore, when the sensor is mounted loosely in the distal end of a relatively long probe, the length of the probe may increase substantially and almost immediately in response to its temperature being increased, whereas the wires coupling the sensors to circuitry at the proximal end of the probe may lengthen at a much slower rate because of the more gradual increase of the temperature of the wires. This situation can result in the wires within the probe becoming so taut that the sensor is displaced within or even pulled from the distal end of the probe as the body of the probe lengthens. On the other hand, if the sensor were fixedly held in the distal end of the probe (e.g., using a high-temperature epoxy), the difference in thermal expansion between the wires and the probe body may lead to excessive loading on the wires so that they may stretch and possibly break. The above-noted problems relating to the difference in thermal expansion rates between the probe body and the connecting wires may be exacerbated over time as the probe apparatus is subjected to several temperature cycles.

Figure 8A:
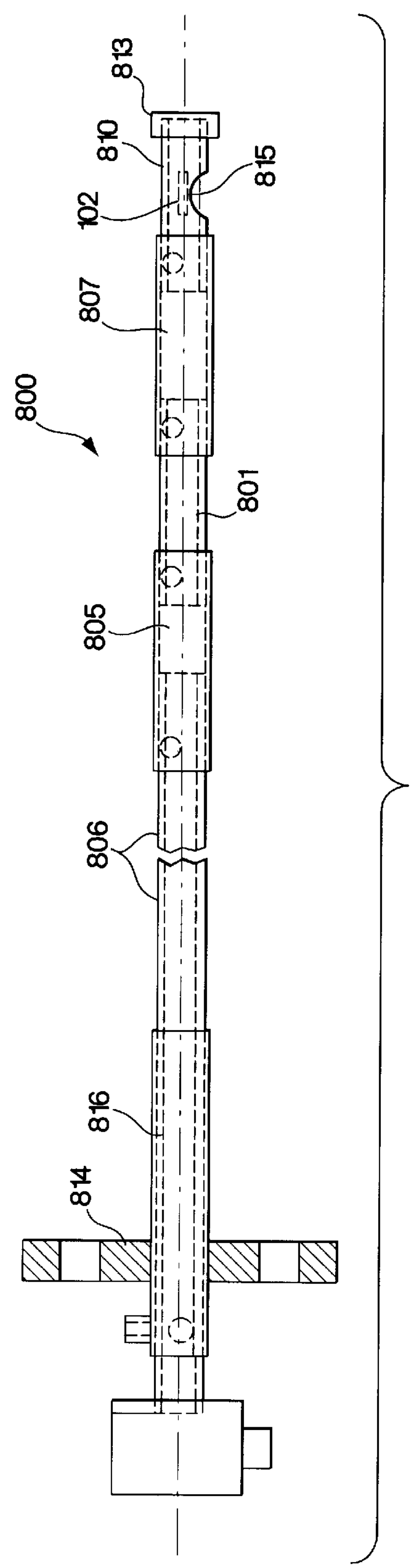
FIGS. 8A–B illustrate examples of specialized probes that may be used to dispose sensors within a combustor according to an aspect of the invention.
Figure 8B:
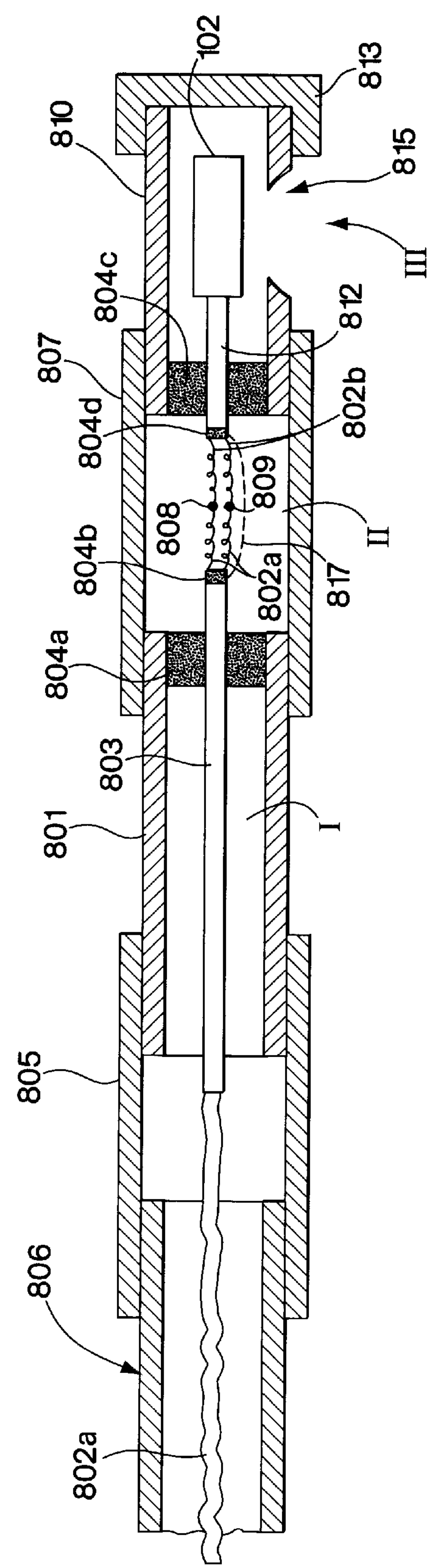

An embodiment of the present invention that overcomes the above-noted drawbacks is illustrated in FIGS. 8A–B. As shown in FIG. 8A, a proximal end (i.e., a connector portion 816) of a probe 800 may be inserted through an opening in a wall 814 of a combustor, e.g., the combustor 100 of FIG. 1A. The connector portion 816 can support a relatively long (e.g., 3, 6, 10, 15, 20 feet or longer) support member (e.g., a section of metal pipe 806). As shown in FIG. 8B, a pair of wires 802*a* may extend along the entire length of the pipe 806. In the embodiment shown, the distal end of the pipe 806 is connected to a proximal end of another, substantially shorter, section of pipe 801 via a connecting sleeve 805. The connections between the connecting sleeve 805 and the pipes 801 and 806 may be accomplished in any of a number of ways, and the invention is not limited in any particular technique for interconnecting the same. In some embodiments, for example, the outer portions of the ends of the pipes 801 and 806, and the inner, end portions of the sleeve 805 may be correspondingly threaded to permit the connection to be formed, or the sections may be interconnected using bolts or the like. In the embodiment shown, a distal end of the pipe 801 is further connected to another section of pipe 810 via another connecting sleeve 807. The connections between the sleeve 807 and the pipes 801 and 810 may be made in a similar manner as the connections between the sleeve 805 and the pipes 801 and 806.

In the embodiment of FIG. 8B, a ceramic isolator 803 is supported within the section of pipe 801 using a quantity of high-temperature epoxy 804a. Similarly, a ceramic isolator 812 is supported within the section of pipe 810 using another quantity of high-temperature epoxy 804*c*. As shown, the wires 802*a* may be fed through the ceramic isolator 803 and pass through a quantity of high-temperature epoxy 804*b* disposed in a distal end of the ceramic isolator 803. Similarly, wires 802*b* from a gas sensor 102 (e.g., a Nernstian-type solid electrolyte oxygen sensor) may be fed through the ceramic isolator 812 and pass through a quantity of high-temperature epoxy 804*d* disposed in a proximal end of the ceramic isolator 812. As illustrated in FIG. 8B, the wires 802*a* passing through the ceramic isolator 803 may be connected to the wires 802*b* passing through the ceramic isolator 812 at a pair of junction points 808 and 809 disposed within a cavity formed by the connecting sleeve 807. Because the distal ends of the wires 802*a* are held stationary with respect to the distal end of the section of pipe 801 by means of the quantity of high-temperature epoxy 804*b*, the substantial thermal expansion of the relatively long pipe 806 cannot cause the gas sensor 102 to be displaced when and if the wires 802*a* become taut. That is, in the embodiment shown, any change in tension in the wires 802*a–b* which is caused by the thermal expansion of the pipe 806 will occur only in the area proximal of the quantity of high-temperature epoxy 804*b*. The expansion of the pipe 806 will not alter the amount of tension in the portions of the wires 802*a–b* between the quantity of high-temperature epoxy 804*b* and the gas sensor 102. To prevent damage to the sensor wires 802*a* proximal of the quantity of high-temperature epoxy 804*b*, the wires 802*a* may be disposed loosely enough in the pipe 806 so that when the pipe 806 is elongated a maximum amount, the wires 802*a* are not stretched to their breaking point.

The difference in thermal expansion between the connecting sleeve 807 and portions of the sensor wires 802*a–b* between the quantity of high-temperature epoxy 804*b* and the quantity of high-temperature epoxy 804*d* may be accommodated by leaving enough slack in the wires 802*a–b* (see dashed line 817) that the maximum amount of expansion of the connecting sleeve 807 will not cause the wires 802*a–b* to stretch to their breaking point. Because the connecting sleeve 807 is relatively short, there need only be a small amount of slack in the wires 802*a–b* to achieve this result.

As illustrated in FIG. 8B, the gas sensor 102 is held in a fixed relationship with respect to the pipe section 810 via the ceramic isolator 812. The difference in thermal expansion between the ceramic isolator 812 and the wires 802*b* disposed therein is small enough that only a minimal amount of slack is required to be left in the portion of the wires 802*b* distal of the quantity of high-temperature epoxy 804*d* to prevent the wires 802*b* from becoming damaged when the probe 800 is subjected to high temperatures. It should be appreciated that the gas sensor 102 may be held in a fixed relationship with respect to a housing (e.g., the pipe 810) at the distal end of the probe 800 in any of numerous alternative ways, and the invention is not limited to the particular technique described. For example, epoxy may be disposed throughout the cavity formed within the pipe 810 or throughout selected portions thereof so as to maintain the fixed relationship between the gas sensor 102 and the pipe 810.

In the embodiment of FIGS. 8A–B, a hole 815 is provided on one side of the pipe 810 to permit gas near the distal end of the probe 800 to access the gas sensor 102. As shown, a cap 813 may be threaded onto (or otherwise attached to) a distal end of the section of pipe 810 so as to create a cavity therein with the hole 815 being the only means accessing the cavity and gas sensor 102 disposed therein.

In one embodiment, the connecting sleeve 807 includes a removable plate (i.e., a cover) attached thereto, for example, using bolts or the like. This cover may be positioned so that a user may remove it to access the connection points 808 and 809 to disconnect the wires 802*a* from the wires 802*b*. After disconnecting the wires in this manner, the user may remove the pipe 810 from the connecting sleeve 807 (e.g., by unscrewing or unbolting these portions from one another), thereby permitting the user to replace the entire sensor housing (including the pipe 810, the ceramic isolator 812, the quantities of high-temperature epoxy 804*c–d*, and the cap 813) from the distal end of the probe 800. This modularity of the sensor-portion of the probe 800 greatly facilitates the replacement of a faulty sensor. It should be appreciated that removable plates may additionally or alternatively be disposed on other portions of the probe 800 (e.g., on the pipe 806, the connecting sleeve 805, the section or pipe 801, etc.) to permit a user to access the connection points 808 and 809 or other connection points of the wires 802*a–b*.

Calibration of a gas sensor 102 disposed at a distal end of a probe may be performed by removing the entire probe 800 from the wall 814 of the combustor in which it is used and calibrating the gas sensor 102 when it is so removed. However, this removal of the probe 800 can be burdensome and time consuming, especially when the combustor is operating because of the high temperatures therein.

Figure 9A:
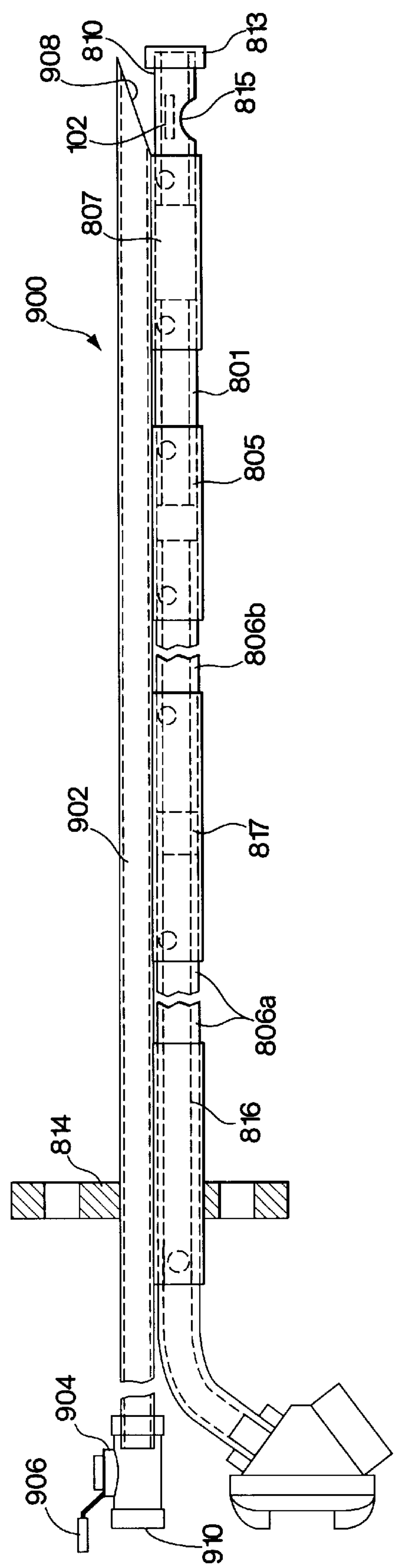
FIGS. 9A shows an illustrative embodiment of a probe such as that shown in FIGS. 8A–B having a calibration tube disposed thereon in accordance with an aspect of the invention.

FIG. 9A illustrates an illustrative embodiment of a probe 900 similar to that shown in FIGS. 8A–B, which has a calibration tube 902 attached to it in accordance with one aspect of the invention. As discussed below, the calibration tube 902 permits the gas sensor 102 disposed in a distal end of the probe 900 (adjacent the hole 815) to be calibrated without requiring the probe 900 to be removed from the wall 814 of the combustor. As shown in FIG. 9A, the probe 900 includes essentially the same components as the probe 800 of FIGS. 8A–B. For convenience in accessing the wires within the main, longer pipe 806, however, an additional connecting sleeve 817 is provided in the FIG. 9A embodiment. The use of the additional connecting sleeve 817 also facilitates the feeding of the wires through the main pipe 806.

As shown in FIG. 9A, the calibration tube 902 may have a valve 904 connected to its proximal end. A handle 906 of the valve 904 may be manipulated to open the valve 904 to place an opening 910 of the valve 904 (adjacent a proximal end of the probe 900) in fluid communication with an opening 908 of the calibration tube 902 (adjacent a distal end of the probe 900). Opening the valve 904 therefore permits gas provided to the opening 910 to pass through the tube 902 to the opening 908, or permits gas near the distal end of the probe 900 to be sampled through the opening 908 and provided at the opening 910. The provision of the calibration tube 902 on the probe 900 permits the gas sensor 102 to be calibrated without removing the probe 900 from the wall 814 of the combustor.

When a sensor such as the sensor 102 described above in connection with FIG. 4 is employed, the sensor 102 may generate a signal responsive only to changes in the concentration of oxygen in the gas being monitored thereby. Therefore, such a sensor cannot be calibrated simply by immersing it in a gas having a constant, known oxygen concentration and adjusting the sensor and/or its output signal accordingly. At least three techniques that may be employed to calibrate this novel type of gas sensor have been identified. While each of these techniques is described below as being used in conjunction with the calibration tube 902 so as not to require the probe 900 to be removed from the wall 814 of the combustor, it should be appreciated that each may alternatively be employed without such a calibration tube, e.g., when the probe is removed from the wall 814 of the combustor, and that the invention is not limited to embodiments that employ such calibration tubes.

Figure 9B:
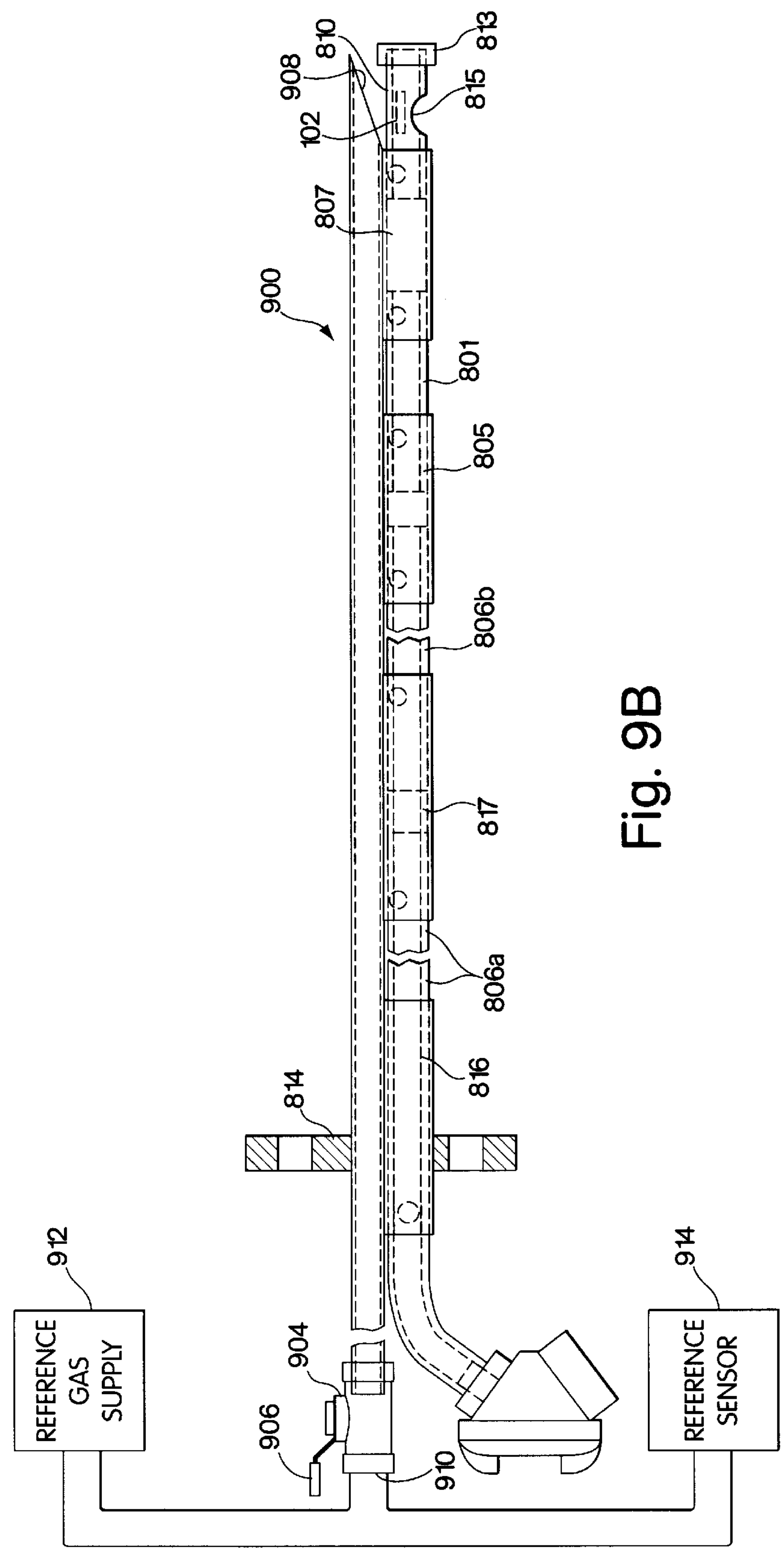
FIGS. 9B–C show two examples of system configurations that may be employed to calibrate a gas sensor using the calibration tube of FIG. 9A.

A first technique that may be employed to calibrate the gas sensor 102 is illustrated in FIG. 9B. As shown, the opening 910 of the valve 904 may be placed in fluid communication with both a reference gas supply 912 and a reference sensor 914 so that a pulse of gas from the reference gas supply 912 may be provided to both the opening 910 (and therefore to the opening 908) and to the reference sensor 914. The reference gas supply 912 and the reference sensor 914 may be located anywhere with respect to the opening 910 so long as each is in fluid communication therewith.

The reference sensor 914 may be any gas sensor capable of generating a signal indicative of the concentration of a particular gas (e.g., oxygen, carbon monoxide, etc.) or of a particular class of gasses (e.g., gaseous combustibles) in an analyzed gas sample. In one embodiment, the reference gas supply 912 is a tank containing gas having a known level of gaseous combustibles therein, and the reference sensor 914 is configured to generate a signal indicative of the level of gaseous combustibles in the gas supplied to it from the reference gas supply 912. One example of a suitable reference sensor 914 is a portable carbon monoxide monitor, model VIA-510, manufactured by Horiba, Inc. of Irvine, Calif. It should be appreciated, however, that the reference sensor 914 may alternatively analyze the gas from the reference gas supply 912 for any of a number of alternative constituents, and that the invention is not limited to the analysis of gas from the reference gas supply 912 for levels of carbon monoxide or other gaseous combustibles therein.

Figure 10:
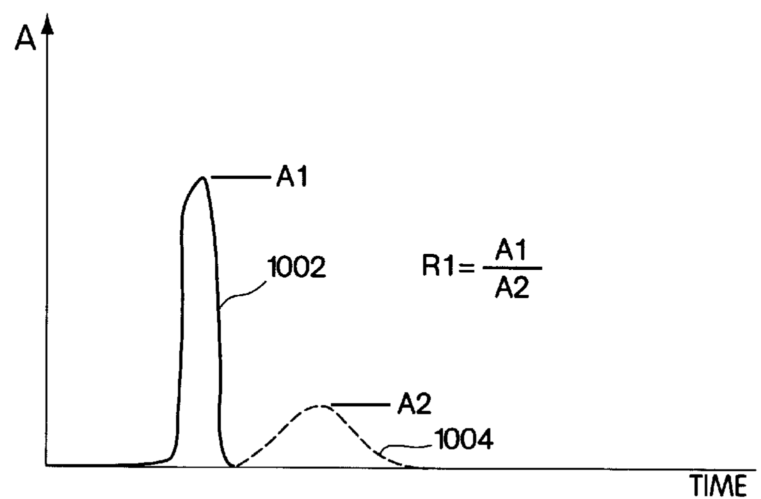
FIG. 10 illustrates signals that may be generated by a gas sensor disposed at a distal end of the calibration tube of FIG. 9B and a reference sensor in fluid communication with a proximal end of the calibration tube of FIG. 9B when calibrating the gas sensor in accordance with one embodiment of the invention.

In the embodiment of FIG. 9B, the gas sensor 102 disposed at the distal end of the probe 900 may be calibrated by feeding a pulse of gas from the reference gas supply 912 simultaneously to the opening 910 of the valve 904 (with the valve 904 open) and to the reference sensor 914. FIG. 10 is a timing diagram illustrating signals 1002 and 1004 that may be generated, respectively, by the gas sensor 102 located adjacent the opening 908 and the reference sensor 914 when a sample of gas having a predetermined concentration of gaseous combustibles is supplied by the reference gas supply 912 to both the opening 910 (with the valve 904 open) and the reference sensor 914 for a predetermined, finite period of time.

As shown in FIG. 10, when gas having the same concentration of combustibles is fed to the gas sensor 102 and the reference sensor 914, the signals 1002 and 1004 generated by the two sensors may be quite different. It has been discovered however, that the peak magnitudes achieved by the signals 1002 and 1004 in response to different pulsed samples of gas are consistently in a particular ratio with one another. In the illustration of FIG. 10, for example, the signals 1002 and 1004 generated by the gas sensor 102 and the reference sensor 914 have peak magnitudes A1 and A2, respectively. Therefore, by recording the ratio of the peak amplitudes A1/A2, the gas sensor 102 at the distal end of the probe 900 may be calibrated at a future time by: (1) again employing an accurate and reliable reference sensor 914 in the system of FIG. 9B, and (2) in response to a pulsed gas sample from the reference gas supply 912, adjusting the gas sensor 102 or processing (e.g., smoothing and/or scaling) the signal 1002 generated thereby until the ratio of the peak amplitudes A1/A2 is equal to the previously recorded value thereof.

Figure 9C:
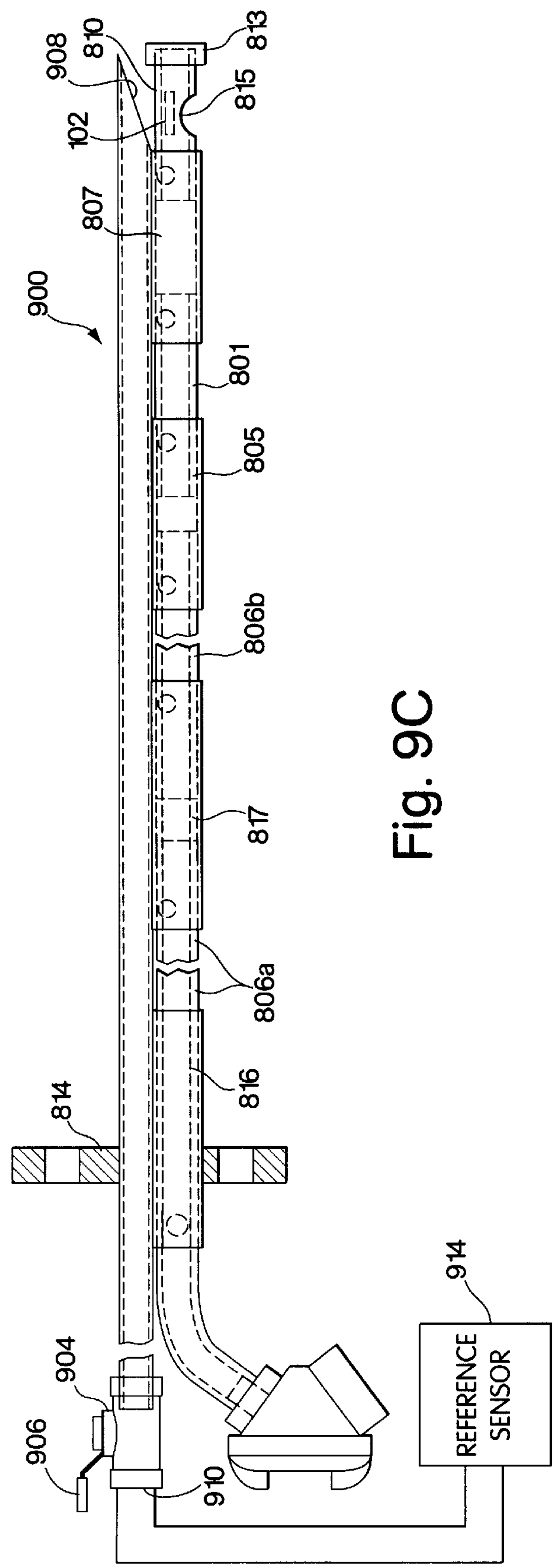

A second technique that may be employed to calibrate the gas sensor 102 is illustrated in FIG. 9C. As shown, the opening 910 of the valve 904 may be placed in fluid communication with the reference sensor 914 so that gas adjacent the distal end of the probe 900 may be sampled via the opening 908 and provided to the reference sensor 914 via the calibration tube 902. The reference sensor 914 may, for example, be the same type of sensor used in connection with the embodiment of FIG. 9B, and may be located anywhere with respect to the opening 910 so long as it is in fluid communication therewith.

In the embodiment of FIG. 9C, the gas sensor 102 disposed at the distal end of the probe 900 may be calibrated by simultaneously monitoring the signals generated by the gas sensor 102 and the reference sensor 914. It has been discovered that, after certain processing (e.g., filtering, phase shifting, and/or scaling), the signal from the gas sensor 102 may be made to approximate the signal from the reference sensor 914. Therefore, the gas sensor 102 may be initially calibrated in this manner, and this initial calibration of the gas sensor 102 may be duplicated in the future by: (1) again employing an accurate and reliable reference sensor 914 in the system of FIG. 9C, and (2) properly adjusting the gas sensor 102 and/or processing the signal generated thereby to again make the signal from the gas sensor 102 approximate the signal from the references sensor 914.

Figure 11:
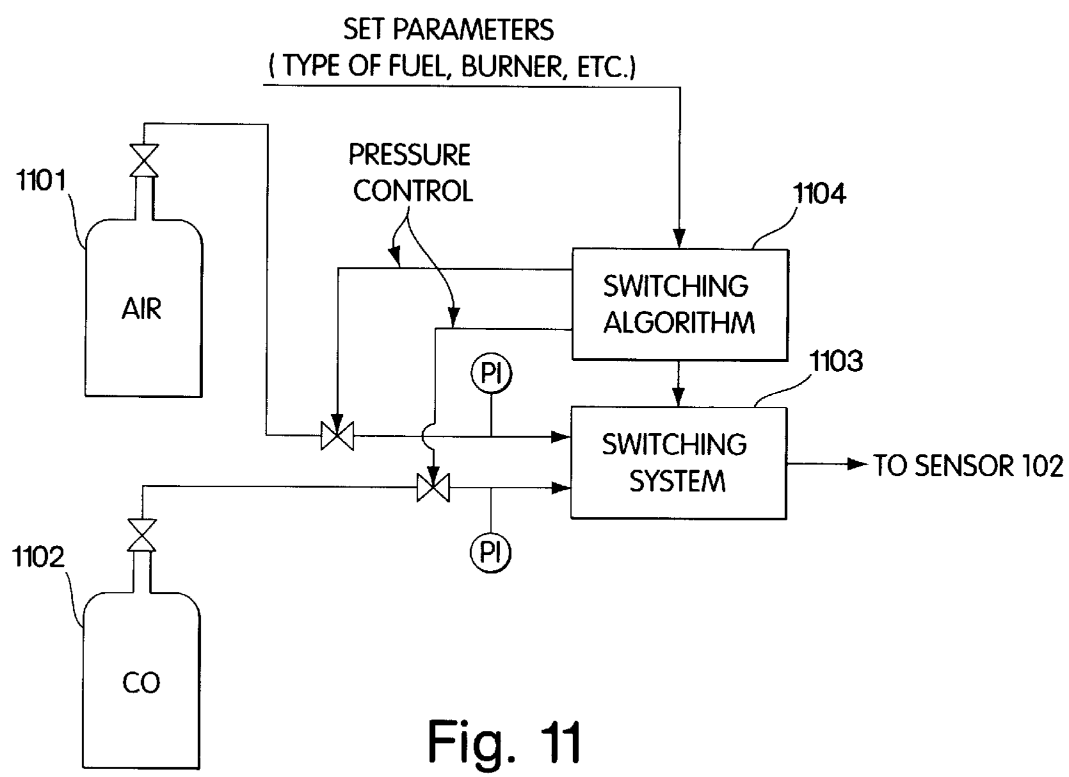
FIG. 11 illustrates an example of a calibration system that may be employed in accordance with an aspect of the present invention.

A third technique that may be employed to calibrate the gas sensor 102 is illustrated in FIG. 11. As shown, two tanks 1101 and 1102 containing different gases (e.g., air and CO) are connected to a switching system 1103. The switching system 1103 may be controlled by sequencer 1104 to supply the two gases to the sensor 102 (not shown) either directly or via the calibration tube 902 (not shown) according to a preselected switching algorithm. The sequencer 1104 simulates real time combustion frequencies and may be adjusted for different types of fuel or boilers. For example, the sequencer 1104 may open on air supply for 1 second, and then open a CO supply (e.g., 0.05%) for 0.1 seconds. The frequency and duration of air and CO openings may be different for different applications, such as different types of fuel, burner or combustion system, and may be adjusted accordingly. In embodiments wherein the sensor 102 is removed from the combustor prior to calibration, the sensor 102 may be maintained within the required temperature range using, for example, an electric heater or oven.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting. The invention is limited only as defined by the following claims and the equivalents thereto.

What is claimed is:

1. A system for monitoring a level of gaseous combustibles in an environment of a fossil combustor which includes at least one continuous-burning combustion device that supplies gaseous emissions into the environment, the system comprising:

a Nernstian-type gas sensor having first and second electrodes disposed on a solid-electrolyte to generate a signal therebetween indicative of a difference between an oxygen concentration at the first electrode and an oxygen concentration at the second electrode, wherein the first and second electrodes are constructed and arranged such that each of the first and second electrodes is in fluid communication with the environment when the system is monitoring the level of gaseous combustibles in the environment; and at least one processor that analyzes the signal to determine the level of gaseous combustibles in the environment.

2. The system of claim 1, further comprising means for restricting fluid flow between the environment and the second electrode so that gas from the environment reaches the second electrode at a slower rate than it reaches the first electrode.

3. The system of claim 1, further comprising a porous substance arranged to at least partially restrict fluid flow between the environment and the second electrode.

4. The system of claim 3, wherein the first electrode does not have any of the porous substance disposed on at least a portion thereof such that the portion of the first electrode is directly exposed to the environment.

5. The system of claim 1, wherein the sensor does not include a temperature control device that eliminates the effect of changes in temperature on the signal generated between the first and second electrodes.

6. The system of any of claims 1–5, in combination with the combustor.

7. The combination of claim 6, wherein the environment is in a post-flame zone of the combustor.

8. A method for monitoring a level of gaseous combustibles in an environment of a fossil combustor which includes at least one continuous-burning combustion device that supplies gaseous emissions into the environment, the method comprising steps of:

(a) providing at least one Nernstian-type gas sensor including a solid-electrolyte, and at least first and second electrodes each disposed on the solid-electrolyte and each in fluid communication with the environment;

(b) generating a signal between the at least first and second electrodes in response to changes in the concentration of oxygen in the environment; and (c) analyzing the signal to determine the level of gaseous combustibles in the environment.

9. The method of claim 8, further comprising a step of:

(d) receiving into the environment a gaseous emission from a post flame zone of the combustor.

10. A method for monitoring a level of gaseous combustibles in an environment of a fossil combustor which includes at least one continuous-burning combustion device that supplies gaseous emissions into the environment, the method comprising steps of:

(a) providing at least one Nernstian-type gas sensor including a mass of material that is permeable to ions formed when gas molecules of at least a first type are ionized, and at least first and second electrodes each arranged on the mass of material and each in fluid communication with the environment;

(b) generating a signal between the at least first and second electrodes in response to changes in the concentration of the gas molecules of the first type in the environment; and (c) analyzing the signal to determine the level of gaseous combustibles in the environment.

11. The method of claim 10, further comprising a step of:

(d) receiving into the environment a gaseous emission from a post-flame zone of the combustor.

12. A method for monitoring a level of gaseous combustibles in an environment of a fossil combustor which includes at least one continuous-burning combustion device that supplies gaseous emissions into the environment, the method comprising steps of:

(a) providing at least one Nernstian-type gas sensor including a solid-electrolyte and at least first and second electrodes disposed on the solid-electrolyte, wherein the at least one sensor does not include a temperature control device that eliminates the effect of changes in temperature on the signal generated between the first and second electrodes;

(b) generating a signal between the at least first and second electrodes in response to changes in the concentration of oxygen in the environment; and (c) analyzing the signal to determine the level of gaseous combustibles in the environment.

13. The method of claim 12, further comprising a step of:

(d) receiving into the environment a gaseous emission from a post flame zone of the combustor.

14. A system for monitoring a level of gaseous combustibles in an environment of a fossil combustor which includes at least one continuous-burning combustion device that supplies gaseous emissions into the environment, the system comprising:

a Nernstian-type gas sensor including first and second electrodes disposed on a solid-electrolyte to generate a signal therebetween indicative of a difference between an oxygen concentration at the first electrode and an oxygen concentration at the second electrode; and at least one processor that analyzes the signal to determine the level of gaseous combustibles in the environment:

wherein the system does not include a temperature control device that eliminates the effect of changes in temperature on the signal generated between the first and second electrodes.

15. The system of claim 14, in combination with the combustor is.

16. The combination of claim 15, wherein the environment is in a post-flame zone of the combustor.

* * * * *